(12) United States Patent
Huggins et al.

(10) Patent No.: US 8,889,695 B2
(45) Date of Patent: Nov. 18, 2014

(54) QUINAZOLINONE COMPOUNDS

(75) Inventors: Penelope Jane Huggins, Murrumbeena (AU); Jack Gordon Parsons, Brunswick (AU)

(73) Assignee: Prana Biotechnology Limited, Victoria (AU)

( * ) Notice: Subject to any disclaimer, the term of this patent is extended or adjusted under 35 U.S.C. 154(b) by 27 days.

(21) Appl. No.: 13/142,162

(22) PCT Filed: Dec. 23, 2009

(86) PCT No.: PCT/AU2009/001701
§ 371 (c)(1),
(2), (4) Date: Aug. 25, 2011

(87) PCT Pub. No.: WO2010/071944
PCT Pub. Date: Jul. 1, 2010

(65) Prior Publication Data
US 2012/0040980 A1    Feb. 16, 2012

(30) Foreign Application Priority Data
Dec. 24, 2008 (AU) .................. 2008906650

(51) Int. Cl.
A01N 43/54 (2006.01)
A61K 31/517 (2006.01)
C07D 239/72 (2006.01)
C07D 401/00 (2006.01)

(52) U.S. Cl.
USPC ..................................... 514/259.4

(58) Field of Classification Search
USPC .................. 544/283, 284; 514/259.4
See application file for complete search history.

(56) References Cited

U.S. PATENT DOCUMENTS

| 8,084,459 B2 | 12/2011 | Kok et al. | |
| 8,163,760 B2 * | 4/2012 | Bush et al. | 514/259.4 |
| 2011/0071167 A1 * | 3/2011 | Bush et al. | 514/259.41 |

FOREIGN PATENT DOCUMENTS

| WO | WO 2005/095360 A1 | 10/2005 |
| WO | WO 2007/118276 A1 | 10/2007 |
| WO | WO 2007/147217 A1 | 12/2007 |
| WO | WO 2008/074068 A1 | 6/2008 |

OTHER PUBLICATIONS

CAS Registry No. 953843-85-1, STN entry date Nov. 15, 2007.
CAS Registry No. 953843-84-0, STN entry date Nov. 15, 2007.
CAS Registry No. 953843-83-9, STN entry date Nov. 15, 2007.
CAS Registry No. 866318-14-1, STN entry date Oct. 27, 2007.
International Search Report dated Feb. 9, 2010 issued in PCT/AU2009/001701.
International Preliminary Report on Patentability dated Apr. 13, 2011 issued in PCT/AU2009/001701.

* cited by examiner

*Primary Examiner* — Paul V. Ward
(74) *Attorney, Agent, or Firm* — Scully, Scott, Murphy & Presser, P.C.

(57) ABSTRACT

The present invention relates to quinazolinone compounds, processes for their preparation and their use as pharmaceutical agents for the treatment of Parkinson's disease (PD). The quinazolinone compounds are of general formula (I).

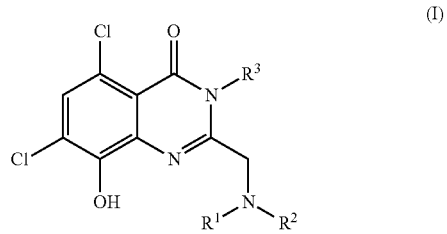

20 Claims, No Drawings

QUINAZOLINONE COMPOUNDS

FIELD

The present invention relates to quinazolinone compounds, processes for their preparation and their use as pharmaceutical agents for the treatment of Parkinson's disease (PD).

BACKGROUND

PD is a progressive illness that is symptomatically characterised by slowness of movement (bradykinesia), rigidity and/or tremor and postural instability. Patients with PD have a deficiency of the neurotransmitter dopamine, due to chronic and progressive degeneration of the substantia nigra in the brain.

The cause of PD is unknown, however the deficiency in dopamine has led to the widespread use of dopamine-replacing agents as symptomatic treatments for the disease. The most commonly prescribed drug for this treatment is L-3,4-dihydroxyphenylalanine (L-dopa) and dopamine agonists.

These symptomatic treatments are successful in increasing the quality of life of patients suffering from PD. Such dopamine-replacement treatments do however have significant limitations, particularly in long-term treatment. These limitations include fluctuations in the efficacy of the treatment, leading to the "on-off" phenomenon and appearance of side-effects which manifest as abnormal involuntary movements.

Other than L-dopa, the most common medicaments for alleviating these motor symptoms are dopamine agonists such asrotigotine, pramipexole, bromocriptine, ropinirole, cabergoline, pergolide, apomorphine and lisuride, anticholinergic agents, N-methyl d-aspartate (NMDA) antagonists, beta-blockers as well as the Monoamine oxidase B (MAO-B) inhibitor selegeline and the Catechol-O-methyl transferase (COMT) inhibitor entacapone.

The majority of these medicaments intervene in the dopaminergic and/or cholinergic signal cascade and symptomatically influence motor disturbances.

Whilst the above symptomatic treatments can enhance the life of a PD patient, often restoring function to nearly normal for some period of time, each have side effects and no treatment provides a cure for the disease. Over time, as the disease progresses, drug dosing must be adjusted to best meet a patient's symptomatic needs.

SUMMARY

The present invention provides quinazoline compounds which are neurologically active and can be used in the treatment of PD.

International Patent Publication No. WO2005/095360 describes heterocyclic compounds having two fused 6-membered rings with nitrogen atoms at positions 1 and 3, a carboxy group at position 4 and a hydroxy group at position 8 with both rings being aromatic. These compounds are useful as pharmaceutical agents, in particular for the treatment of neurological conditions, more specifically neurodegenerative conditions such as Alzheimer's disease (AD).

We have now developed heterocyclic compounds having two fused 6-membered rings with nitrogen atoms at positions 1 and 3, a carboxy group at position 4, a hydroxy group at position 8 and substituents at the 2 and 3 positions.

These compounds fall within the generic scope of International Patent Publication No. 2005/095360, but are not specifically disclosed therein.

While not wishing to be bound by any theory, it is believed that the nature of the substituents at positions 2 and 3 may be important making them useful in the treatment of PD. Particularly, substituents at these positions are established to provide superior management of biologically available ionic iron (Fe), which has been identified in high concentrations within the region of the human brain associated with (PD)—the substantia nigra (SN). In response to an unidentified trigger in PD, Fe levels in neurons of the SN rise significantly. This rise in Fe is believed to be associated with the generation of damaging reactive oxygen species (ROS) and may be a factor contributing to loss of the dopamine producing cells of the SN, which is the key neuropathological feature of PD. The inventors have identified that the compounds of the present invention are specifically capable of associating principally with Fe, acting to prevent its excessive uptake by neuronal cells and lowering its intracellular concentration.

The action of the compounds of the present invention differs from the treatment of other neurological diseases, such as AD. Compounds employed for AD are designed to associate principally with the ionic metals copper (Cu) and zinc (Zn). These particular metals have been demonstrated to be closely bound within plaque deposits of the protein beta amyloid (Abeta), a hallmark of AD pathology. The sequestering and removal of Cu and Zn is considered to reduce their availability for interaction with Abeta, inhibiting that protein's toxicity and tendency to form plaques. Compounds for treatment of AD have further been demonstrated to display the function of transporting Cu and/or Zn into neuronal cells. In AD, such transported metals have been demonstrated to influence (decrease) the processing of the parent molecule APP, which is cleaved to produce Abeta, as seen in Alzheimer plaques and to promote expression of enzymes which degrade Abeta. The compounds of the present invention have alternatively been selected to preferentially not facilitate cellular metal uptake.

In one aspect, there is provided a compound of general formula I

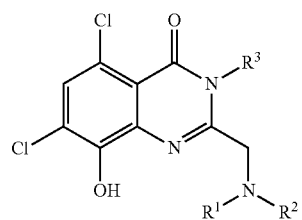

in which $R^1$ and $R^2$ are independently selected from H, optionally substituted $C_{1-6}$alkyl, optionally substituted $C_{3-6}$cycloalkyl and optionally substituted $C_{2-6}$alkynyl provided that at least one of $R^1$ and $R^2$ is other than H; or $R^1$ and $R^2$ together with the N atom to which they are attached form an optionally substituted 5- or 6-membered heterocyclyl which may contain at least one further heteroatom selected from N and O; and $R^3$ is selected from optionally substituted $C_{1-6}$alkyl and optionally substituted $C_{3-6}$cycloalkyl or pharmaceutically acceptable salts thereof, with the provisos that:
(a) when $R^1$ and $R^2$ are methyl, then $R^3$ is not $CH_2CH(CH_3)_2$; and
(b) when $R^1$ is H and $R^2$ is methyl, then $R^3$ is not methyl, propyl or cyclopropyl.

The invention also provides a process for the preparation of the compound of formula I defined above which comprises the steps of:

(a) cyclisation of a compound of formula III in the presence of a source of a leaving group

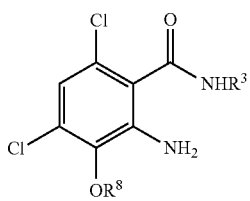

in which
R³ is as defined above; and
R⁸ is H or a protecting group
to prepare a compound of formula IV

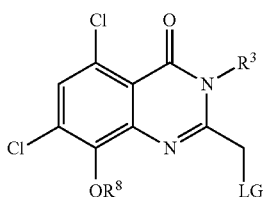

in which
R³ and R⁸ are as defined above; and
LG is a leaving group; and (b) aminating the compound of formula IV with a source of NR¹R² and deprotecting when R⁸ is a protecting group.

The invention alternatively provides a process for the preparation of the compound of formula I defined above which comprises the steps of:

(i) cyclisation of a compound of formula V in the presence of a source of NR³

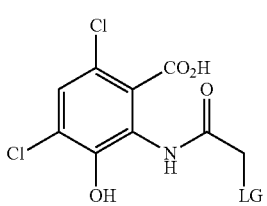

in which
R³ is as defined above; and
LG is a leaving group to prepare a compound of formula VI

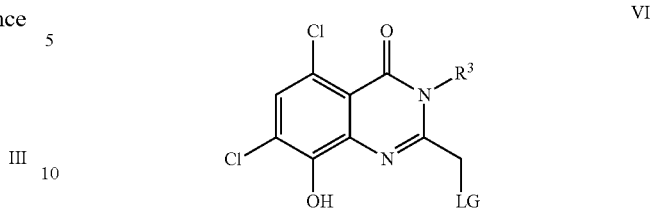

in which
R³ and LG are as defined above; and (ii) aminating the compound of formula VI with a source of NR¹R² in which R¹ and R² are as defined above.

The invention further provides use of the compound of formula I defined above as a pharmaceutical agent, preferably a neurotherapeutic or neuroprotective agent, more preferably an agent for the treatment of Parkinson's disease.

The compound of formula I is advantageously administered in the form of a pharmaceutical composition together with a pharmaceutically acceptable carrier.

In a second aspect, there is provided a pharmaceutical composition comprising the compound of formula I defined above and a pharmaceutically acceptable carrier.

In a third aspect, there is provided a method for the treatment of Parkinson's disease which comprises administering an effective amount of a compound of general formula II

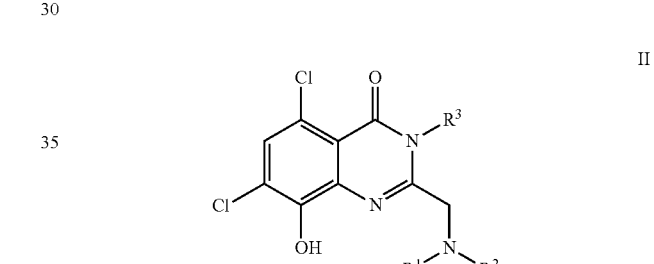

in which
$R^1$ and $R^2$ are independently selected from H, optionally substituted $C_{1-6}$alkyl and optionally substituted $C_{2-6}$alkynyl provided that at least one of $R^1$ and $R^2$ is other than H; or $R^1$ and $R^2$ together with the N atom to which they are attached form an optionally substituted 5- or 6-membered heterocyclyl which may contain at least one further heteroatom selected from N and O; and
$R^3$ is selected from optionally substituted $C_{1-6}$alkyl and optionally substituted $C_{3-6}$cycloalkyl
or pharmaceutically acceptable salts thereof.

There is also provided use of the compound of formula II defined above for the treatment of Parkinson's disease.

There is further provided use of the compound of formula II defined above in the manufacture of a medicament for the treatment of Parkinson's disease.

There is still further provided the compound of formula II defined above for use in the treatment of Parkinson's disease.

DETAILED DESCRIPTION

The present invention relates to neurologically active compounds that are useful for the treatment of Parkinson's disease.

The present invention provides a compound of general formula I

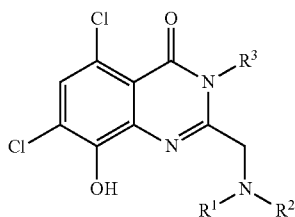

I

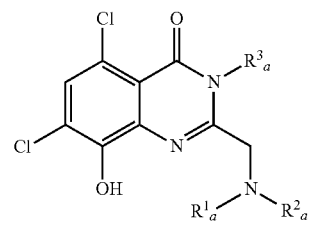

Ia in which
R$^1$ and R$^2$ are independently selected from H, optionally substituted C$_{1-6}$alkyl, optionally substituted C$_{3-6}$cycloalkyl and optionally substituted C$_{2-6}$alkynyl provided that at least one of R$^1$ and R$^2$ is other than H; or R$^1$ and R$^2$ together with the N atom to which they are attached form an optionally substituted 5- or 6-membered heterocyclyl which may contain at least one further heteroatom selected from N and O; and R$^3$ is selected from optionally substituted C$_{1-6}$alkyl and optionally substituted C$_{3-6}$cycloalkyl or pharmaceutically acceptable salts thereof, with the provisos that:
(a) when R$^1$ and R$^2$ are methyl, then R$^3$ is not CH$_2$CH(CH$_3$)$_2$; and
(b) when R$^1$ is H and R$^2$ is methyl, then R$^3$ is not methyl, propyl or cyclopropyl.

In one embodiment, there is provided the compound of formula I defined above, with the further proviso that:
(c) when R$^1$ and R$^2$ are methyl and R$^3$ is methyl, ethyl or methylene cyclopropyl, then pharmaceutically acceptable salts of formula I are excluded.

In an alternative embodiment, there is provided the compound of formula I defined above, with the further proviso that:
(c) when R$^1$ and R$^2$ are methyl, then R$^3$ is not methyl, ethyl or methylene cyclopropyl.

In another embodiment, there is provided the compound of formula I defined above, with the further provisos that:
(d) when R$^1$ is H and R$^2$ is ethyl, then R$^3$ is not ethyl; and
(e) when R$^1$ is H and R$^2$ is ethyl, then R$^3$ is not C$_{1-2}$alkyl.

The optional substituents are preferably selected from C$_{1-4}$alkyl, optionally substituted aryl, halo, optionally substituted C$_{3-6}$cycloalkyl and optionally substituted 5- or 6-membered heterocyclyl containing at least one heteroatom selected from N and O.

Preferably R$^3$ is selected from methyl substituted with C$_{3-6}$cycloalkyl or methyl substituted with optionally substituted 5- or 6-membered heterocyclyl containing at least one heteroatom selected from N and O; substituted C$_{2-6}$alkyl and optionally substituted C$_{3-6}$cycloalkyl.

Preferably R$^1$ is H and R$^2$ is selected from C$_{3-6}$alkyl, substituted C$_{1-6}$alkyl, optionally substituted C$_{1-6}$alkyl and optionally substituted C$_{2-6}$alkynyl.

Preferably R$^1$ is C$_{1-6}$alkyl and R$^2$ is selected from C$_{2-6}$alkyl, C$_{1-6}$ substituted alkyl and C$_{2-6}$alkynyl.

Preferably R$^1$ and R$^2$ together with the N atom to which they are attached form an optionally substituted 5- or 6-membered heterocyclyl which may contain at least one further heteroatom selected from N and O.

In one embodiment, the compounds of formula I have the formula Ia in which
R$^1{}_a$ is selected from H and C$_{1-4}$alkyl;
R$^2{}_a$ is selected from C$_{1-4}$alkyl, C$_{2-6}$alkynyl and C$_{1-4}$alkyl substituted with optionally substituted aryl; or
R$^1{}_a$ and R$^2{}_a$ together with the N atom to which they are attached form an optionally substituted 5- or 6-membered heterocyclyl which may contain at least one further heteroatom selected from N and O; and
R$^3{}_a$ is C$_{1-4}$alkyl
or pharmaceutically acceptable salts thereof,
with the proviso that when R$^1{}_a$ and R$^2{}_a$ are methyl, then R$^3{}_a$ is not CH$_2$CH(CH$_3$)$_2$.

In another embodiment, the compounds of formula I have the formula Ia defined above, with the proviso that when R$^1{}_a$ is H and R$^2{}_a$ is ethyl, then R$^3{}_a$ is not C$_{1-2}$alkyl.

Preferably R$^2{}_a$ is selected from C$_{3-4}$alkyl, C$_{2-6}$alkynyl and C$_{1-4}$alkyl substituted with optionally substituted aryl.

Preferably R$^1{}_a$ and R$^2{}_a$ together with the N atom to which they are attached form an optionally substituted saturated 5- or 6-membered heterocyclyl which may contain at least one further heteroatom selected from N and O.

Representative examples of compounds of formula Ia are as follows:

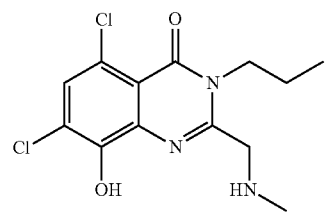

F4495

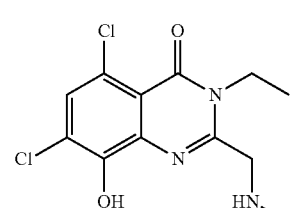

F4486

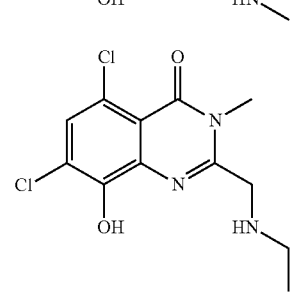

F4496

-continued
F4386
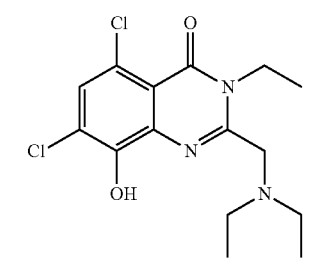
F4392
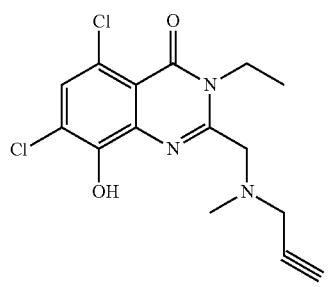
F4473
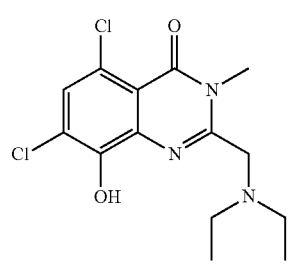
F4475
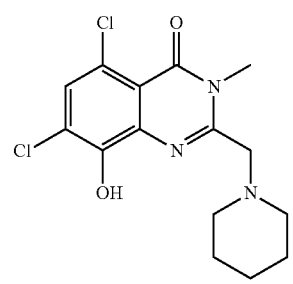
F4477
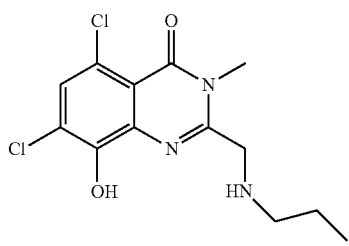
F4483
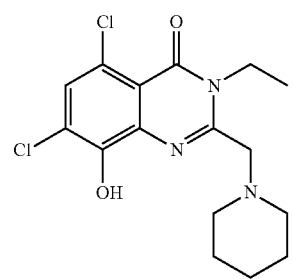
-continued
F4487
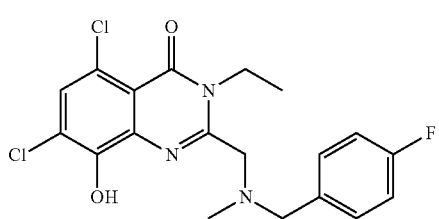
F4492
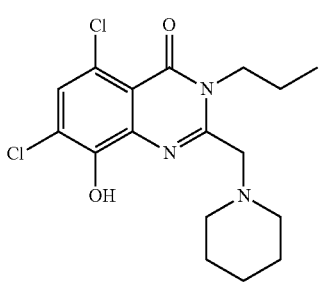
F4551
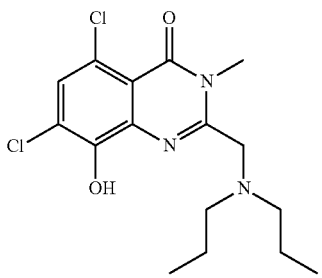
F4549
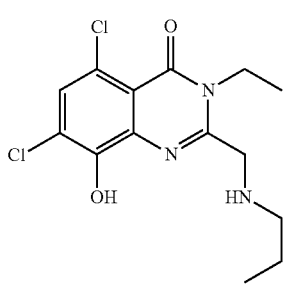
F4550
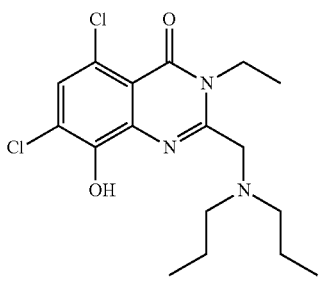
F4530
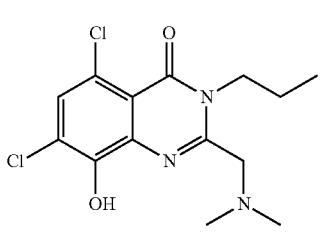

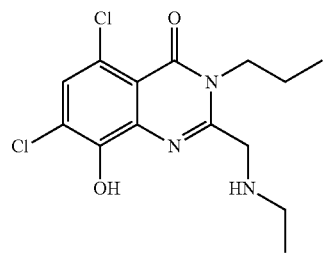 F4540
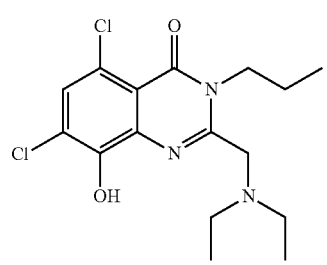 F4541
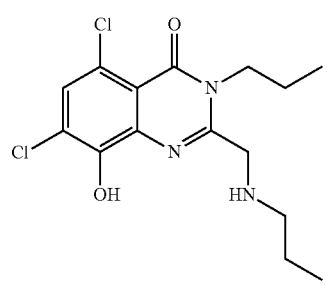 F4542
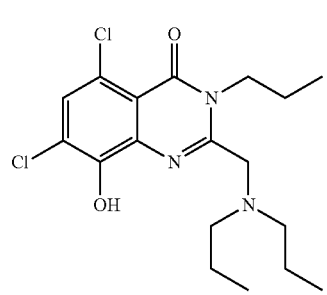 F4543
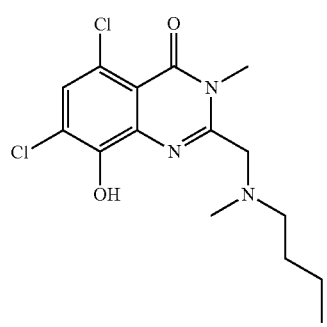 F4552
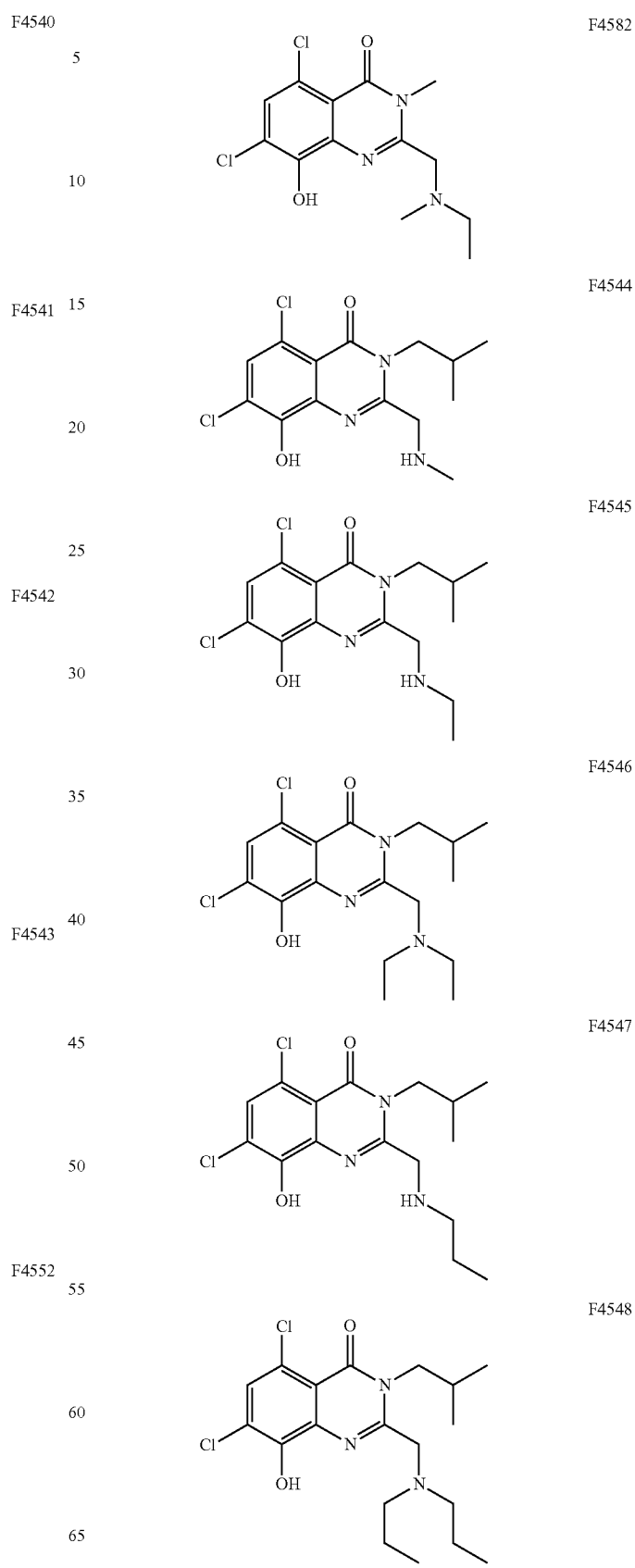

| F4553 | F4B |
| F4554 | F4C |
| F4555 | F4D |
| F4552 | F4E |
| F4582 | |
| F4A | F4F |

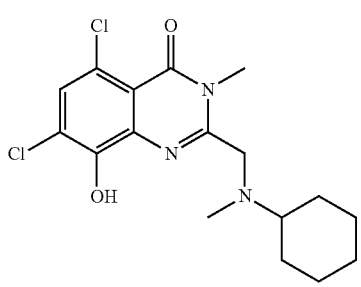

F4G or pharmaceutically acceptable salts thereof.

Preferred examples of compounds of formula Ia include F4495, F4486 and F4496, more preferably F4496.

In another embodiment, the compounds of formula I have the formula Ib

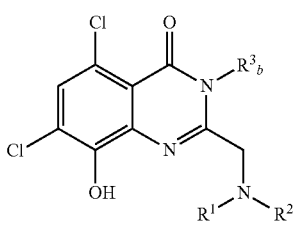

Ib in which
$R^1$ and $R^2$ are as defined above; and
$R^3_b$ is optionally substituted $C_{3-6}$cycloalkyl
or pharmaceutically acceptable salts thereof.

Preferably $R^1$ and $R^2$ are independently selected from $C_{1-4}$alkyl.

In a further embodiment, the compounds of formula I have the formula Ic

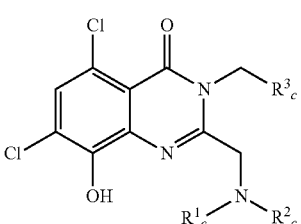

Ic in which
$R^1_c$ is selected from H and $C_{1-4}$alkyl;
$R^2_c$ is selected from $C_{1-4}$alkyl, $C_{3-6}$cycloalkyl, methyl substituted with optionally substituted aryl and $C_{2-4}$alkynyl; or
$R^1_c$ and $R^2_c$ together with the N atom to which they are attached form an optionally substituted 5- or 6-membered heterocyclyl which may contain at least one further heteroatom selected from N and O; and
$R^3_c$ is selected from optionally substituted $C_{3-6}$cycloalkyl, optionally substituted aryl and optionally substituted 5- or 6-membered heterocyclyl containing at least one heteroatom selected from N and O
or pharmaceutically acceptable salts thereof.

Preferably aryl in $R^2_c$ and $R^3_c$ is optionally substituted with halo.

Preferably $R^1_c$ is H and $R^2_c$ is $C_{3-4}$alkyl.

Preferably $R^1_c$ is $C_{1-6}$alkyl and $R^2_c$ is selected from $C_{1-6}$alkyl and $C_{2-6}$alkynyl.

Representative examples of compounds of formula Ic are as follows:

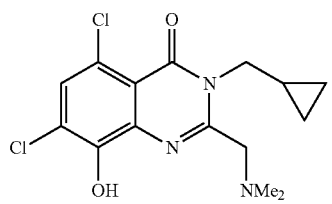 [SMILES: CN(C)Cc1nc2c(O)c(Cl)cc(Cl)c2c(=O)n1CC1CC1]

F4267

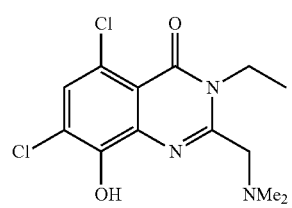

F4268

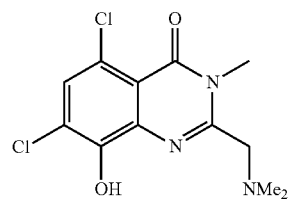

F4269

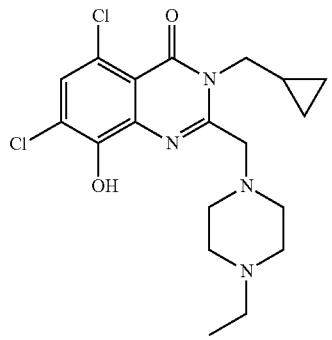

F4383

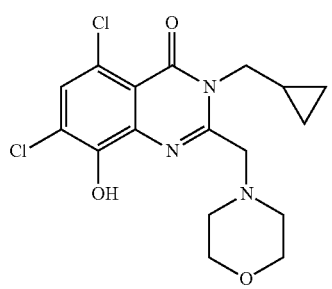 [SMILES: O=c1c2c(Cl)cc(Cl)c(O)c2nc(CN2CCOCC2)n1CC1CC1]

F4384

F4385 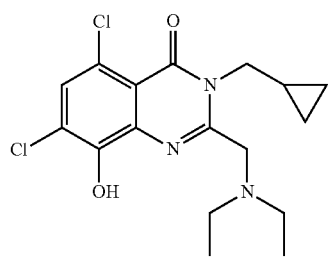 [SMILES: CCN(CC)Cc1nc2c(O)c(Cl)cc(Cl)c2c(=O)n1CC1CC1]
F4387 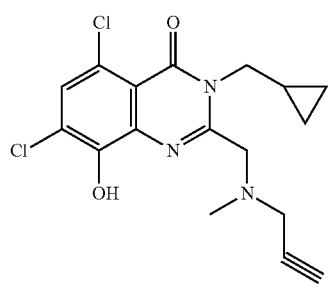
F4391 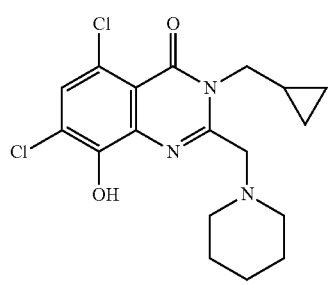 [SMILES: O=c1c2c(Cl)cc(Cl)c(O)c2nc(CN2CCCCC2)n1CC1CC1]
F4480 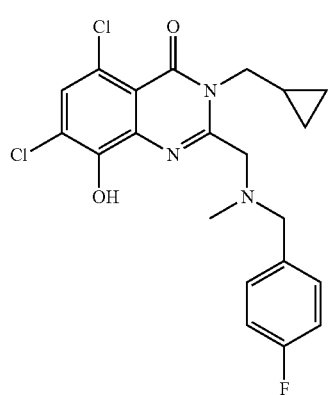 [SMILES: CN(Cc1ccc(F)cc1)Cc1nc2c(O)c(Cl)cc(Cl)c2c(=O)n1CC1CC1]
F4499 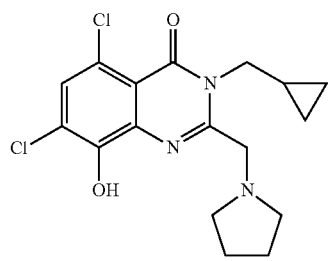 [SMILES: O=c1c2c(Cl)cc(Cl)c(O)c2nc(CN2CCCC2)n1CC1CC1]
F4536 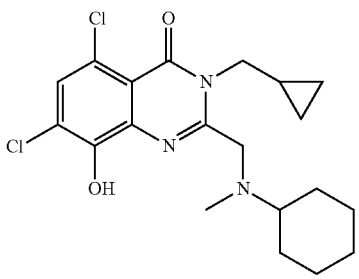
F4535 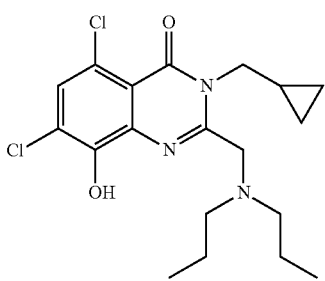 [SMILES: CCCN(CCC)Cc1nc2c(O)c(Cl)cc(Cl)c2c(=O)n1CC1CC1]
F4581 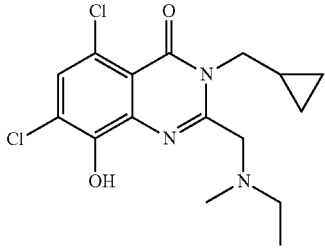
F4H 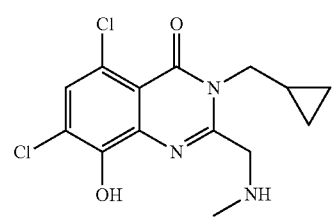 [SMILES: CNCc1nc2c(O)c(Cl)cc(Cl)c2c(=O)n1CC1CC1]
F4I 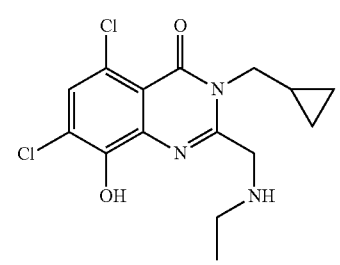 [SMILES: CCNCc1nc2c(O)c(Cl)cc(Cl)c2c(=O)n1CC1CC1]
F4J 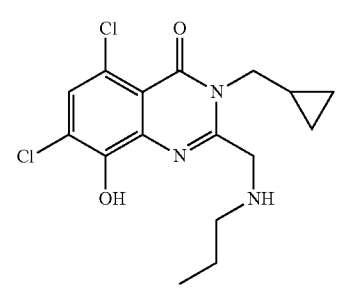 [SMILES: CCCNCc1nc2c(O)c(Cl)cc(Cl)c2c(=O)n1CC1CC1]
or pharmaceutically acceptable salts thereof.

The present invention also provides a method for the treatment of Parkinson's disease which comprises administering an effective amount of a compound of general formula II

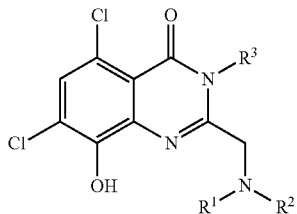

in which
$R^1$ and $R^2$ are independently selected from H, optionally substituted $C_{1-6}$alkyl and optionally substituted $C_{2-6}$alkynyl provided that at least one of $R^1$ and $R^2$ is other than H; or $R^1$ and $R^2$ together with the N atom to which they are attached form an optionally substituted 5- or 6-membered heterocyclyl which may contain at least one further heteroatom selected from N and O; and
$R^3$ is selected from optionally substituted $C_{1-6}$alkyl and optionally substituted $C_{3-6}$cycloalkyl
or pharmaceutically acceptable salts thereof.

Representative examples of compounds of formula II in addition to those of formulae Ia and Ic above include the following

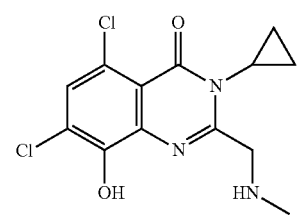
F4062

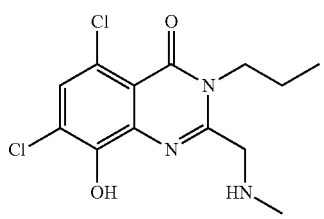
F4095

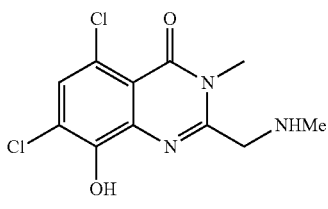
F4161

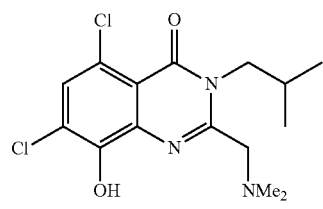
F4271 or pharmaceutically acceptable salts thereof.

The term "$C_{1-6}$alkyl" refers to straight chain or branched chain hydrocarbon groups having from 1 to 6 carbon atoms. Examples include ethyl, propyl, isopropyl, butyl, isobutyl, sec-butyl, tert-butyl, pentyl, neopentyl and hexyl.

The term "$C_{1-6}$alkylene" refers to the divalent equivalent of "$C_{1-6}$alkyl" defined above.

The term "$C_{2-6}$alkynyl" refers + to straight chain or branched chain hydrocarbon groups having at least one triple bond and 2 to 4 carbon atoms. Examples include ethynyl, 1- or 2-propynyl, 1-, 2- or 3-butynyl and methyl-2-propynyl.

The term "$C_{3-6}$cycloalkyl" refers to non-aromatic cyclic hydrocarbon groups having from 3 to 6 carbon atoms. Examples include cyclopropyl, cyclobutyl, cyclopentyl and cyclohexyl.

The term "aryl" refers to single, polynuclear, conjugated or fused residues of aromatic hydrocarbons. Examples include phenyl, biphenyl, terphenyl, quaterphenyl, naphthyl, tetrahydronaphthyl, anthracenyl, dihydroanthracenyl, benzanthracenyl, dibenxanthracenyl and phenanthrenyl. 6-membered aryls such as phenyl are preferred.

The term "5- or 6-membered heterocyclyl" refers to saturated or unsaturated monocyclic hydrocarbon groups containing at least one heteroatom atom selected from the group consisting of N and O.

Suitable heterocyclyls include N-containing heterocyclic groups, such as, unsaturated 5- or 6-membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

saturated 5 or 6-membered heteromonocyclic groups containing 1 to 3 nitrogen atoms, such as, pyrrolidinyl, imidazolidinyl, piperidinyl or piperazinyl;

unsaturated 5- to 6-membered heteromonocyclic group containing an oxygen atom, such as, pyranyl or furyl;

unsaturated 5 or 6-membered heteromonocyclic group containing 1 to 2 oxygen atoms and 1 to 3 nitrogen atoms, such as, oxazolyl, isoxazolyl or oxadiazolyl; and saturated 5- or 6-membered heteromonocyclic group containing 1 to 2 oxygen atoms and 1 to 3 nitrogen atoms, such as, morpholinyl.

Preferred heterocyclyls include piperidinyl, piperazinyl, morpholinyl, pyridinyl, pyrazolyl, imidazolyl and tetrazolyl.

The term "halo" refers to fluorine, chlorine, bromine and iodine, preferably fluorine.

The term "optionally substituted" refers to a group that may or may not be further substituted with one or more groups selected from $C_{1-6}$ alkyl, Si($C_{1-6}$alkyl)$_3$, $C_{3-6}$ cycloalkyl, $C_{2-6}$ alkenyl, $C_{2-6}$ alkynyl, aryl, heterocycylyl, halo, halo$C_{1-6}$alkyl, halo$C_{3-6}$cycloalkyl, halo$C_{2-6}$alkenyl, halo$C_{2-6}$alkynyl, haloaryl, haloheterocyclyl, hydroxy, $C_{1-6}$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$, alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{2-6}$alkenylacyl, $C_{2-6}$alkynylacyl, arylacyl, heterocycylylacyl, acylamino, acyloxy, aldehydro, $C_{1-6}$alkylsulfonyl, arylsulfonyl, $C_{1-6}$alkylsulfonylamino, arylsulphonylamino, $C_{1-6}$alkylsulfonyloxy, arylsulfonyloxy, $C_{1-6}$alkylsulfenyl, $C_{2-6}$alklysulfenyl, arylsulfenyl, carboalkoxy, carboaryloxy, mercapto, $C_{1-6}$alkylthio, arylthio, acylthio, cyano, phosphorus-containing groups and the like. Preferred optional substituents are selected from $C_{1-4}$alkyl, optionally substituted aryl, halo, optionally substituted $C_{3-6}$cycloalkyl and optionally substituted 5- or 6-membered heterocyclyl containing at least one heteroatom selected from N and O.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety. Preferred salts are acid addition salts of pharmaceutically acceptable inorganic acids such as hydrochloric or hydrobromic acid addition salts.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF) and the like with the solvate forming part of the crystal lattice by either non-covalent binding or by occupying a hole in the crystal lattice. Hydrates are formed when the solvent is water, or alcoholates are formed when the solvent is alcohol. Solvates of the compounds of the present invention can be conveniently prepared or formed during the processes described herein. In addition, the compounds of the present invention can exist in unsolvated as well as solvated forms. In general, the solvated forms are considered equivalent to the unsolvated forms for the purposes of the compounds and methods provided herein.

Additionally, the compounds of the present invention can exist in unsolvated as well as solvated forms with pharmaceutically acceptable solvents such as water, ethanol, and the like. The solvated forms of the compounds of the present invention are also considered to be disclosed herein.

Where a compound possesses a chiral center the compound can be used as a purified enantiomer or diastereomer, or as a mixture of any ratio of stereoisomers. It is however preferred that the mixture comprises at least 70%, 80%, 90%, 95%, 97.5% or 99% of the preferred isomer.

This invention also encompasses prodrugs of the compounds of formula I.

The term "pro-drug" is used herein in its broadest sense to include those compounds which are converted in vivo to the compound of formula I. Use of the pro-drug strategy optimises the delivery of the drug to its site of action, for example, the brain. In one embodiment, compounds of formula I having free amino, amido, hydroxy or carboxylic acid groups can be converted into prodrugs. Prodrugs include compounds wherein carbonates, carbamates, amides and alkyl esters which are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of compounds of formula I. Prodrugs may also include N-oxides, and S-oxides of appropriate nitrogen atoms in formula I.

In another embodiment, prodrugs include the presence of a $C_{1-6}$ alkyl or arylester moiety which is designed to resist hydrolysis until the pro-drug has crossed the BBB, where esterases on the inner surface of the BBB act to hydrolyse the ester and liberate the C8 hydroxyl of the compound of formula I.

Process of Making Compounds

Compounds of the general formula I are generally prepared by cyclising the compound of formula III. The cyclisation may be performed using any suitable known technique for example, dehydrative cyclisation involving chloroacetylchloride.

The products formed from either reaction step may be further derivatised using techniques known to those skilled in the art. Alternatively, derivatisation of the mono-halo intermediate may be undertaken prior to reaction of the second halo substituent. Those skilled in the art will appreciate that the order of the reactions described for the syntheses above may be changed in certain circumstances and that certain functionalities may need to be derivatised (i.e. protected) in certain instances for the reactions described above to proceed with reasonable yield and efficiency. The types of protecting functionalities are well known to those skilled in the art and are described for example in Greene (Greene, T., Wuts, P. (1999) Protective Groups in Organic Synthesis. Wiley-Interscience; 3rd edition).

Examples of protecting groups which may be used to protect a hydroxy group include, but are not limited to, silyl groups (eg trimethylsilyl, t-butyldimethylsilyl, t-butyldiphenylsilyl), benzyl groups (eg benzyl, methoxybenzyl, nitrobenzyl, benzyl halides such as benzyl bromide or benzyl chloride), alkyl groups (eg methyl, ethyl, n- and i-propyl, and n-, sec- and t-butyl) and acyl groups (e.g. acetyl such as acetyl chloride or acetyl anhydride and benzoyl).

The leaving group may be any suitable known type such as those disclosed in J. March, "Advanced Organic Chemistry: Reactions, Mechanisms and Structure" $4^{th}$ Edition, pp 352-357, John Wiley & Sons, New York, 1992 which is incorporated herein by reference. Preferably, the leaving group is halogen, more preferably chlorine.

Pharmaceutical Compositions

The present invention provides pharmaceutical compositions comprising at least one of the compounds of the formula I and a pharmaceutically acceptable carrier. The carrier must be "pharmaceutically acceptable" means that it is compatible with the other ingredients of the composition and is not deleterious to a subject. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy*, 21st Ed., 2005, Lippincott Williams & Wilkins).

The compounds of the invention may be administered by any suitable means, for example, orally, such as in the form of tablets, capsules, granules or powders; sublingually; buccally; parenterally, such as by subcutaneous, intravenous, intramuscular, intra(trans)dermal, or intracisternal injection or infusion techniques (e.g., as sterile injectable aqueous or non-aqueous solutions or suspensions); nasally such as by inhalation spray or insufflation; topically, such as in the form of a cream or ointment ocularly in the form of a solution or suspension; vaginally in the form of pessaries, tampons or creams; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

The pharmaceutical compositions for the administration of the compounds of the invention may conveniently be presented in dosage unit form and may be prepared by any of the methods well known in the art of pharmacy. These methods generally include the step of bringing the compound of formula I into association with the carrier which constitutes one or more accessory ingredients. In general, the pharmaceutical compositions are prepared by uniformly and intimately bringing the compound of formula I into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the compound of formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents such as sweetening agents, flavouring agents, colouring agents and preserving agents, e.g. to provide pharmaceutically stable and palatable preparations. Tablets contain the compound of formula I in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the compound of formula I is mixed with an inert solid diluent, for example, calcium carbonate, calcium phosphate or kaolin, or as soft gelatin capsules wherein the compound of formula I is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of formula I in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the compound of formula I in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For administration to the respiratory tract, including intranasal administration, the active compound may be administered by any of the methods and formulations employed in the art for administration to the respiratory tract.

Thus in general the active compound may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose and carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the subject administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of active compound may be controlled by provision of a metered valve.

Alternatively the active compound may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the active compound will generally have a small particle size, for example of the order of 5 microns or less. Such a particle size may be obtained by means known in the art, for example by micronisation.

When desired, formulations adapted to give sustained release of the active compound may be employed.

The active compound may be administered by oral inhalation as a free-flow powder via a "Diskhaler" (trade mark of Glaxo Group Ltd) or a meter dose aerosol inhaler.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions suitable for vaginal administration may be presented as pessaries, tampons, creams, gels, pastes, foams or sprays containing in addition to the active ingredient such carriers as are known in the art to be appropriate.

For topical use, creams, ointments, jellies, solutions or suspensions, etc., containing the compounds of the present invention are employed. (For purposes of this application, topical application shall include mouthwashes and gargles.)

For application to the eye, the active compound may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride, or chlorhexidine and thickening agents such as hypromellose may also be included.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

Efficacy of this class of compounds may be applicable to drug eluting stents. Potential applications of drug eluting stents with these compounds include pulmonary artery stenosis, pulmonary vein stenosis, as well as coronary artery stenosis. Drug eluting stents may also be used in saphenous vein grafts or arterial grafts or conduits. Drug eluting stents that release this class of compounds may also be applicable for treating stenoses of the aorta or peripheral arteries, such as the iliac artery, the femoral artery or the popliteal artery. The compound may be bound to the drug eluting stent by any of various methods known in the field. Examples of such methods include polymers, phosphoryl choline, and ceramics. The compound may also be impregnated into a bioabsorbable stent.

The active compounds may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) rectally or intravaginally, e.g. as a pessary, cream or foam.

The pharmaceutical composition and method of the present invention may further comprise other therapeutically active compounds as noted herein which are usually applied in the treatment of neurological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include dopamine-replacing agents and dopamine agonists such asrotigotine, pramipexole, bromocriptine, ropinirole, cabergoline, pergolide, apomorphine and lisuride, anticholinergic agents, NMDA antagonists, beta-blockers as well as the MAO-B inhibitor selegeline and the COMT inhibitor entacapone.

When other therapeutic agents are employed in combination with the compounds of the present invention they may be used for example in amounts as noted in the Physician Desk Reference (PDR) or as otherwise determined by one of ordinary skill in the art.

Methods of Treatment

The compounds of formula I may be used in the treatment of Parkinson's disease.

Generally, the term "treatment" means affecting a subject, tissue or cell to obtain a desired pharmacological and/or physiological effect and include: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The term "subject" refers to any animal having a disease which requires treatment with the compound of formula I.

In addition to primates, such as humans, a variety of other mammals can be treated using the compounds, compositions and methods of the present invention. For instance, mammals including, but not limited to, cows, sheep, goats, horses, dogs, cats, guinea pigs, rats or other bovine, ovine, equine, canine, feline, rodent or murine species can be treated. However, the invention can also be practiced in other species, such as avian species (e.g., chickens).

The term "administering" should be understood to mean providing a compound of the invention to a subject in need of treatment.

Dosages

The term "therapeutically effective amount" refers to the amount of the compound of formula I that will elicit the biological or medical response of a tissue, system, animal or human that is being sought by the researcher, veterinarian, medical doctor or other clinician.

In the treatment or prevention of conditions which require kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The dosage may be selected, for example to any dose within any of these ranges, for therapeutic efficacy and/or symptomatic adjustment of the dosage to the patient to be treated. The compounds will preferably be administered on a regimen of 1 to 4 times per day, preferably once or twice per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLES

The invention will now be described in detail by way of reference only to the following non-limiting examples.

For clarity, compounds of this invention are referred to by number, for example 1-4 and 2-3. The structures of the example compounds so referred to are given in Tables 1-7.

In Examples 1 to 7, the following reference is cited:

White et al., J Neuroscience, (1998) 18, 6207-6217.

Example 1

Scheme 1

A range of 2,3-disubstituted 8-hydroxy-3H-quinazolin-4-ones 4-9 can be prepared by the synthetic route depicted in Scheme 1. Commercially available 2,4-dichlorobenzoic acid 1-1 is nitrated to give 2,4-dichloro-5-nitrobenzoic acid 1-2. Nitro compound 1-2 is reduced with tin(II)chloride to provide aniline 1-3 which in turn is converted to the acetamide 1-4. A second nitration provides intermediate 1-5, subsequent base hydrolysis affords phenol 1-6. Amide 2-10 is produced in the presence of an amine and activating agent, EDC. The reaction is noteworthy in that the phenol does not require protection. Amide 2-10 is allowed to react with Fe powder in glacial acetic acid to give amine 2-11. Reaction with chloroacetyl chloride followed by condensation reaction with $PCl_3$ affords chloromethyl compound 4-15. Finally, amination with a secondary amine and HCl formation provides the desired target compounds 4-9.

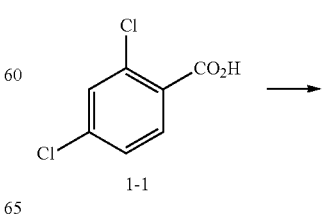

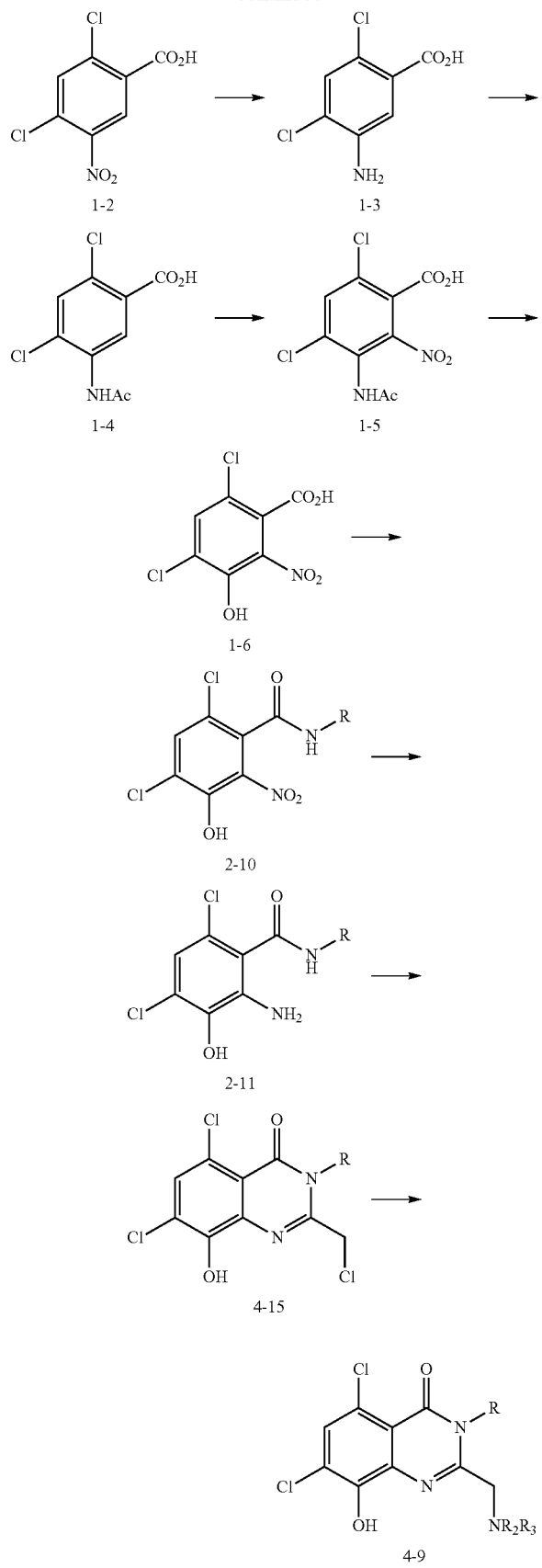

2,4-Dichloro-5-nitrobenzoic acid (1-2)

2,4-Dichlorobenzoic acid 1-1 (1.0 g, 5.34 mmol) was added in one portion to a stirred solution of concentrated nitric acid (0.26 mL, 5.75 mmol) in concentrated sulphuric acid (7 mL). After 3 hours at room temperature the solution was poured onto ice. The resulting white solid was isolated via filtration and washed with $H_2O$ (×3). The white solid was then stirred with 1% $Na_2CO_3$ (aq) (20 mL) for 1 h at room temperature. Remaining insoluble material was filtered off and the resulting clear filtrate was concentrated to a pale yellow solid. Recrystallisation from $H_2O$ afforded the sodium salt as pale yellow crystals. (Note: the other minor product, sodium 2,4-dichloro-3-nitrobenzoate, remained in solution). The yellow crystals of sodium 2,4-dichloro-5-nitrobenzoate was dissolved in a minimum amount of $H_2O$ and acidified by the slow addition of concentrated HCl until a white precipitate formed. After isolation by filtration and washing with $H_2O$ 2,4-dichloro-5-nitrobenzoic acid 1-2 was obtained as a white solid (0.91 g, 72%). $^1$H NMR (400 MHz, $CDCl_3$) δ7.73 (s, 1H), 8.60 (s, 1H).

2,4-Dichloro-5-aminobenzoic acid (1-3)

Tin(II) Chloride hydrate (50 g, 0.29 mol) was added to a solution of 2,4-dichloro-5-nitrobenzoic acid 1-2 (10.0 g, 0.045 mol) in EtOH (200 mL). The mixture was stirred for 70° C. for 30 min, cooled and poured onto ice. The pH of the mixture was adjusted to 8 using saturated aqueous $NaHCO_3$. The suspension was left to stir at room temperature for 5 h and re-acidified to pH 5 with glacial AcOH. The resulting white suspension was continuously washed with EtOAc, the extracts combined, washed with brine, dried over $Na_2SO_4$, filtered and concentrated to afford the desired amine 1-3 as an off-white solid (8.8 g, 96%). $^1$H NMR (400 MHz, $CD_3OD$) δ7.27 (s, 1H), 7.30 (s, 1H).

5-Acetamido-2,4-dichlorobenzoic acid (1-4)

Acetic anhydride (27 mL) was added to 2,4-dichloro-5-aminobenzoic Acid 1-3 (8.0 g, 0.041 mol) in glacial AcOH (150 mL). The solution was stirred at room temperature for 30 min and concentrated to yield the desired acetamide 1-4 as a white solid (9.6 g, 96%). $^1$H NMR (400 MHz, $CD_3OD$) δ2.19 (s, 3H), 7.62 (s, 1H), 8.32 (s, 1H).

3-Acetamido-4,6-dichloro-2-nitrobenzoic acid (1-5)

5-Acetamido-2,4-dichlorobenzoic acid 1-4 (40.0 g, 0.161 mol) was added in portions to a cooled mixture of concentrated $H_2SO_4$ (400 mL) and concentrated nitric acid (400 mL) at 5° C. After stirring for 2 h concentrated $H_2SO_4$ (100 mL)/concentrated nitric acid (100 mL) was added. After another 90 min concentrated $H_2SO_4$ (400 mL)/concentrated nitric acid (200 mL) was added and stirring was continued for a further 2 h. The reaction mixture was cautiously poured onto ice resulting in the formation of a yellow precipitate. The product was collected by filtration then extracted into EtOAc. The combined organic layers were washed with $H_2O$, brine, dried over $Na_2SO_4$, filtered and concentrated to provide the nitro compound 1-5 as a yellow/orange solid (38.1 g, 81% yield). $^1$H NMR (400 MHz, d6-DMSO) δ1.99 (s, 3H), 8.21 (s, 1H), 10.27 (s, 1H).

4,6-Dichloro-3-hydroxy-2-nitrobenzoic acid (1-6)

A solution of KOH (73.4 g,) in $H_2O$ (330 mL) was added to 3-acetamido-4,6-dichloro-2-nitrobenzoic acid 1-5 (38.1 g, 0.130 mol). The resulting brown solution was heated to reflux for 18 h (bath temp 130° C.). The reaction was cooled and extracted with ether. The aqueous layer was then acidified to pH 2 with concentrated HCl and extracted into EtOAc (×4). The combined organic layers were washed with brine (×3), dried over $Na_2SO_4$, filtered and concentrated to provide 4,6-dichloro-3-hydroxy-2-nitrobenzoic acid 1-6 as a brown solid (31.0 g, 95%). $^1$H NMR (400 MHz, d6-DMSO) δ7.88 (s, 1H).

4,6-Dichloro-N-cyclopropylmethyl-3-hydroxy-2-nitrobenzamide (2-10, R=cyclopropylmethyl))

The 4,6-dichloro-3-hydroxy-2-nitrobenzoic acid 1-6 (5.03 g, 19.9 mmol) was dissolved in anhydrous $CH_2Cl_2$ (60 mL) and anhydrous THF (30 mL) then treated with EDC (4.61 g, 24.0 mmol), (aminomethyl)cyclopropane (2.35 mL, 27.1 mmol) and DIEA (4.18 mL, 24.0 mmol). The reaction was stirred overnight at room temperature then diluted with $CH_2Cl_2$ and 0.5M HCl (aq). The product was extracted into $CH_2Cl_2$ (×4). The organic layer was washed with sat.aq $NaHCO_3$, brine, dried over $Na_2SO_4$, filtered and concentrated to afford the amide 2-10 as a brown foam (3.40 g, 56% crude yield). $^1$H NMR (400 MHz, d6-DMSO) δ0.17 (m, 2H), 0.32 (m, 2H), 0.93 (m, 1H), 3.0 (t, J=8 Hz, 2H), 7.16 (s, 1H), 8.38 (br t, J=8.0 Hz, 1H).

2-Amino-4,6-dichloro-N-cyclopropylmethyl-3-hydroxy-benzamide (2-11, R=cyclopropylmethyl)

The amide 2-10 (10.1 g, 33.1 mmol) was dissolved in glacial AcOH (180 mL) then treated with Fe powder (11.2 g, 0.2 mol) and heated to 80° C. under nitrogen for 1.5 h. The beige suspension was treated with sat. aq $NaHCO_3$ until clear then filtered through celite washing with EtOH. The filtrate was concentrated then extracted into EtOAc (×4). The organic layer was washed with brine, dried over $Na_2SO_4$, filtered, concentrated and triturated with ether/petrol (1:10). The amine 2-11 was collected by filtration as dark brown solid (6.8 g, 75%). $^1$H NMR (400 MHz, d6-DMSO) δ0.21 (m, 2H), 0.39 (m, 2H), 1.18 (m, 1H), 3.10 (t, J=8.0 Hz, 2H), 4.93 (br s, 2H), 6.84 (s, 1H), 8.42 (br t, J=8.0 Hz, 1H).

5,7-Dichloro-2-chloromethyl-3-cyclopropylmethyl-8-hydroxy-3H-quinazolin-4-one (4-15, R=cyclopropylmethyl)

The amine 2-11 (6.8 g, 24.7 mmol) in anhydrous $CH_2Cl_2$ (85 mL) was treated with chloroacetyl chloride (4.5 mL, 56.5 mmol) at 0° C. under $N_2$. The reaction was warmed to room temperature for 30 min then diluted with ether (30 mL)/petrol (100 mL). The resulting brown precipitate was collected by filtration, washing with petrol and dried to provide the chloromethylacetamide intermediate as a brown powder (6.4 g, 74%). $^1$H NMR (400 MHz, d6-DMSO) δ 0.18 (m, 2H), 0.38 (m, 2H), 1.26 (m, 1H), 3.04 (t, J=8.0 Hz, 2H), 4.19 (s, 2H), 7.52 (s, 1H), 8.18 (s, 1H), 9.67 (s, 1H), 10.07 (br s, 1H). To a suspension of the chloromethylacetamide (2.59 g, 7.37 mmol) in toluene (73 mL) was added $PCl_3$ (1.93 mL, 22.1 mmol). The reaction was heated to vigorous reflux under Ar for 2.5 h. Cooled and concentrated in vacuo. Added $H_2O$ (10 mL) then sat. aq $NaHCO_3$ (2 mL) until ph 5-6. Added EtOAc and sonicated well, transferring the mixture into a separating funnel. Extracted into EtOAc (×4), dried over $Na_2SO_4$, filtered, concentrated and purified by FC eluting with 20% EtOAc/petrol to provide the desired chloromethyl compound 4-15 as a light orange solid (771 mg, 31%). $^1$H NMR (400 MHz, d6-DMSO) δ0.41 (m, 4H), 1.22 (m, 1H), 3.97 (d, J=4.4 Hz, 2H), 4.81 (s, 2H), 7.57 (s, 1H), 10.39 (s, 1H).

F4267

Chloromethyl derivative 4-15 (917 mg, 2.75 mmol) was dissolved in anhydrous $CH_2Cl_2$ (25 mL) cooled to 0° C. then treated with dimethylamine (7.5 mL, 15.0 mmol, 2.0M solution in MeOH). The reaction was allowed to warm to room temperature overnight then concentrated and extracted into $CH_2Cl_2$ washing with sat. aq. $NaHCO_3$. The aqueous layer was further extracted with $CH_2Cl_2$ (×3). The combined organic layers were dried over $Na_2SO_4$, filtered and concentrated. The resulting oil was taken up in MeOH (50 mL) and treated with conc. HCl (1.5 mL). After concentrating the solution the resulting yellow solid was pumped dry and then triturated with MeOH (3 mL)/ether (70 mL) to precipitate F4267 (820 mg, 79%) as pale yellow solid that was collected by filtration (See Table 1 for Analysis).

TABLE 1

Compounds prepared according to Example 1 (Scheme 1)

| Compound | Structure | MW | $^1$H NMR | Mass Spec |
| --- | --- | --- | --- | --- |
| F4267 | 5,7-dichloro-8-hydroxy-3-cyclopropylmethyl-2-((dimethylamino)methyl)quinazolin-4(3H)-one | Parent: 342.2  HCl salt: 378.7 | $^1$H NMR (400 MHz, d6-DMSO) δ 0.48 (m, 4H), 1.19 (t, J = 4.80 Hz, 1H), 2.94 (s, 3H), 2.95 (s, 3H), 3.85 (d, J = 6.8 Hz, 2H), 4.86 (d, J = 4.80 Hz, 2H), 7.63 (s, 1H), 8.68 (br s,1H) | m/z 342.1, 344.1 [M + H]$^+$ |
| F4268 | 5,7-dichloro-3-ethyl-8-hydroxy-2-((dimethylamino)methyl)quinazolin-4(3H)-one HCl | Parent: 316.2  HCl salt: 352.6 | $^1$H NMR (400 MHz, d6-DMSO) δ 1.24 (t, J = 7.2 Hz, 3H), 2.96 (s, 3H), 2.97 (s, 3H), 3.91 (q, J = 7.2 Hz, 2H), 4.79 (d, J = 5.2 Hz, 2H), 7.64 (s, 1H), 10.21 (s, 1H), 10.51 (s, 1H). | m/z 316.1, 318.0 [M + H]$^+$ |

TABLE 1-continued

Compounds prepared according to Example 1 (Scheme 1)

| Compound | Structure | MW | $^1$H NMR | Mass Spec |
| --- | --- | --- | --- | --- |
| F4383 | 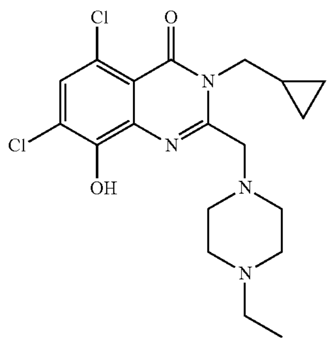 | Parent: 411.3 bis HCl salt: 484.3 | $^1$H NMR (400 MHz, D$_2$O) δ 0.20 (d, J = 4.0 Hz, 2H), 0.39 (d, J = 4.8 Hz, 2H), 0.96 (m, 1H), 1.17 (t, J = 7 Hz, 3H), 3.03 (q, J = 7.0, 4.0 Hz, 2H), 3.30 (br m, 8H), 3.78 (d, J = 4.0 Hz, 2H), 4.06 (s, 2H), 7.04 (s, 1H). | m/z 411.2, 413.2 [M + H]$^+$ |
| F4384 | 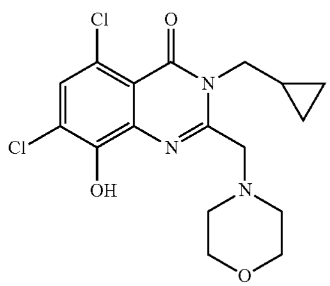 | Parent: 384.3 HCl salt: 420.7 | $^1$H NMR (400 MHz, d6-DMSO) δ 0.48 (m, 4H), 1.21 (m, 1H), 3.59 (d, J = 4.8 Hz, 2H), 3.90 (d, J = 4.0 Hz, 2H), 3.97 (d, J = 4.8 Hz, 2H), 4.15 (t, J = 4.8 Hz, 2H), 4.85 (s, 2H), 7.62 (s, 1H), 10.58 (s, 1H), 10.87 (br s, 1H). | m/z 411.2, 413.2 [M + H]$^+$ |
| F4385 | 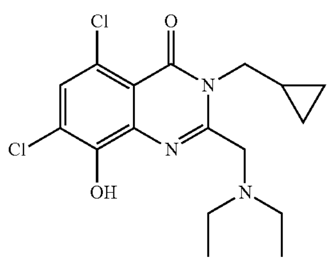 | Parent: 370.3 HCl salt: 406.7 | $^1$H NMR (400 MHz, d6-DMSO) δ 0.43 (m, 2H), 1.17 (t, J = 7.6 Hz, 2H), 1.20 (m, 1H), 1.29 (t, J = 7.2 Hz, 3H), 2.86 (m, 2H), 3.15 (partially obscured), 3.92 (d, J = 7.2 Hz, 2H), 4.76 (d, J = 4.8 Hz, 2H), 7.65 (s, 1H), 10.10 (s, 1H), 10.81 (s, 1H). | m/z 370.1, 372.2 [M + H]$^+$ |
| F4386 | 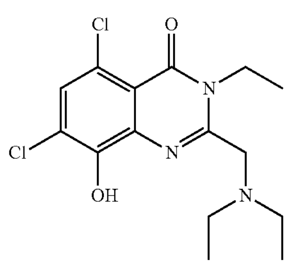 | Parent: 344.2 HCl salt: 380.7 | $^1$H NMR (400 MHz, d6-DMSO) δ 1.25, (t, J = 7.2 Hz), 1.30 (t, J = 7.2 Hz, 3H), 4.71 (d, J = 4.0 Hz, 2H), 3.38 (partially obscured), 3.96 (q, J = 7.2, 4.0 Hz, 2H), 7.65 (s, 1H), 9.66 (s, 1H), 10.63 (s, 1H). | m/z 344.0, 346.1 [M + H]$^+$ |
| F4387 | 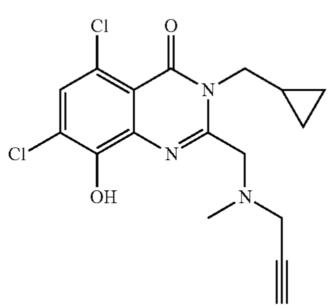 | Parent: 366.2 HCl salt: 402.7 | $^1$H NMR (400 MHz, d6-DMSO) δ 0.46 (d, J = 4.4 Hz, 2H), 0.52 (d, J = 7.2 Hz, 2H), 1.18 (m, 1H), 3.03 (br s, 3H), 3.90 (m, 2H), 3.98 (s, 1H), 4.32 (s, 2H), 4.84 (s, 2H), 7.66 (s, 1H), 10.51 (s, 1H), 10.68 (s, 1H). | m/z 366.1, 368.1 [M + H]$^+$ |

TABLE 1-continued

Compounds prepared according to Example 1 (Scheme 1)

| Compound | Structure | MW | ¹H NMR | Mass Spec |
|---|---|---|---|---|
| F4391 | (5,7-dichloro-8-hydroxy-3-(cyclopropylmethyl)-2-(piperidin-1-ylmethyl)quinazolin-4(3H)-one) | Parent: 382.3<br>HCl salt: 418.7 | ¹H NMR (400 MHz, d6-DMSO) δ 0.53 (m, 4H), 1.19 (m, 1H), 1.43 (m, 1H), 1.72 (m, 1H), 1.81 (m, 2H), 2.06 (m, 2H), 3.18 (m, 2H), 367 (m, 2H), 3.92 (d, J = 7.0 Hz, 4.80 (s, 2H), 7.61 (s, 1H), 10.18 (br s, 1H), 10.65 (s, 1H). | m/z 382.4, 384.4 |
| F4392 | (5,7-dichloro-3-ethyl-8-hydroxy-2-((methyl(prop-2-yn-1-yl)amino)methyl)quinazolin-4(3H)-one) | Parent: 340.2<br>HCl salt: 376.7 | ¹H NMR (400 MHz, d6-DMSO) δ 1.24 (t, J = 7.2 Hz, 3H), 3.03 (s, 3H), 3.96 (m, 3H), 4.30 (s, 2H), 4.80 (s, 2H), 7.65 (s, 1H), 10.50 (s, 1H), 10.65 (br s, 1H). | m/z 340.1, 342.1 [M + H]⁺ |
| F4480 | (5,7-dichloro-3-(cyclopropylmethyl)-2-(((4-fluorobenzyl)(methyl)amino)methyl)-8-hydroxyquinazolin-4(3H)-one) | Parent: 436.31<br>HCl salt: 472.8 | ¹H NMR (400 MHz, d6-DMSO) δ 0.37 (d, J = 4.4 Hz, 2H), 0.46 (d, J = 7.6 Hz, 2H), 1.07 (m, 1H), 2.96 (d, J = 4.4 Hz, 3H), 3.79 (m, 2H), 4.48 (app t, J = 4.4 Hz, 2H), 4.73 (s, 2H), 7.20 (app t, J = 8.4 Hz, 2H), 7.60 (s, 1H), 7.64 (app t, J = 7.2 Hz, 2H), 10.23 (br s, 1H), 10.51 (s, 1H). | m/z 436.4, 438.4 [M + H]⁺ |
| F4499 | (5,7-dichloro-3-(cyclopropylmethyl)-8-hydroxy-2-(pyrrolidin-1-ylmethyl)quinazolin-4(3H)-one) | Parent: 368.3<br>HCl salt: 404.7 | ¹H NMR (400 MHz, d6-DMSO) δ 0.45 (d, J = 3.6 Hz, 2H), 0.48 (d, J = 7.2 Hz, 2H), 1.21 (m, 1H), 2.05 (br m, 4H), 3.26 (m, 2H), 3.74 (m, 2H), 3.86 (d, J = 8.0 Hz, 2H), 4.90 (d, J = 4.2 Hz, 2H), 7.65 (s, 1H), 10.51 (s, 1H), 10.58 (br s, 1H) | m/z 368.4, 370.4 [M + H]⁺ |
| F4535 | (5,7-dichloro-3-(cyclopropylmethyl)-2-((dipropylamino)methyl)-8-hydroxyquinazolin-4(3H)-one) | Parent: 398.33<br>HCl salt: 434.79 | 1HNMR (400 MHz, d6-DMSO) δ 0.41-0.48 (m, 4H), 1.19 (m, 1H), 1.73 (m, 4H), 3.19 (m, 4H), 3.86 (d, J = 7.2 Hz, 2H), 4.74 (s, 2H), 7.60 (s, 1H), 10.18 (bs, 1H), 10.77 (s, 1H) | m/z 400.2 [M + H]⁺, 402.2 |

TABLE 1-continued

Compounds prepared according to Example 1 (Scheme 1)

| Compound | Structure | MW | ¹H NMR | Mass Spec |
|---|---|---|---|---|
| F4536 | 5,7-dichloro-8-hydroxy-3-(cyclopropylmethyl)-2-{[methyl(cyclohexyl)amino]methyl}quinazolin-4(3H)-one | Parent: 410.34 HCl salt: 446.80 | 1H NMR (d6-DMS0, 400 MHz) 0.50 (m, 4H), 1.08 (t, J = 6.8 Hz, 2H), 1.21 (m, 5H), 1.58 (m, 2H), 1.79 (m, 2H), 2.17 (m, 2H), 2.93 (s, 3H), 3.92 (s, 2H), 4.48 (m, 1H), 4.87 (d, J = 16.8 Hz, 1H), 7.66 (s, 1H), 9.82 br m, 1H), 10.78 (d, J = 11.6 Hz, 1H). | ES + ve 410.5, 412.4 [M + H]⁺ |
| F4581 | 5,7-dichloro-8-hydroxy-3-(cyclopropylmethyl)-2-{[methyl(ethyl)amino]methyl}quinazolin-4(3H)-one | Parent: 356.25 HCl salt: 392.71 | 1H NMR (500 MHz, d6-DMSO) δ 0.46-0.53 (m, 4H), 1.23 (m, 1H), 1.37 (t, J = 7.0 Hz, 3H), 2.95 (d, 4J = 5.0 Hz, 3H), 3.33 (m, 1H), 3.41 (m, 1H), 3.91 (d, J = 7.0 Hz, 2H), 4.74 (dd, 2J = 17.0, 4J = 6.0 Hz, 1H), 4.88 (dd, 2J = 17.0, 4J = 4.0 Hz, 1H), 7.65 (s, 1H), 10.39 (bs. 1H), 10.70 (s, 1H). | m/z 356.3, 358.3 [M + H]⁺ |
| F4H | 5,7-dichloro-8-hydroxy-3-(cyclopropylmethyl)-2-[(methylamino)methyl]quinazolin-4(3H)-one | Parent: 328.19 | | |
| F4I | 5,7-dichloro-8-hydroxy-3-(cyclopropylmethyl)-2-[(ethylamino)methyl]quinazolin-4(3H)-one | Parent: 342.22 | | |
| F4J | 5,7-dichloro-8-hydroxy-3-(cyclopropylmethyl)-2-[(propylamino)methyl]quinazolin-4(3H)-one | Parent: 356.25 | | |

Example 2

Scheme 2
A range of novel 2,3-disubstituted 8-hydroxy-3H-quinazolin-4-ones 4-9 can be prepared by the synthetic route depicted in Scheme 2. Nitro acid 1-6 prepared according to Scheme 1 shown in Example 1 is selectively methylated at the carboxy group using iodomethane in DMF to afford methyl ester 1-7. Conversion to the methyl ether 2-2 is achieved by heating 1-7 in acetone and iodomethane. Hydrolysis of 2-2 by heating in NaOH and methanol affords the acid 2-1. Acid chloride formation followed by reaction with an amine provides intermediate 4-5 in good to excellent yields. Reduction with Fe powder in glacial acetic acid gives the amine 4-6 which in turn is cyclised to 4-7 in refluxing AcOH and chloroacetylchloride. Amination of 4-7 followed by deprotection with either $BBr_3$ in $CH_2Cl_2$ or refluxing HBr affords target compound 4-9.

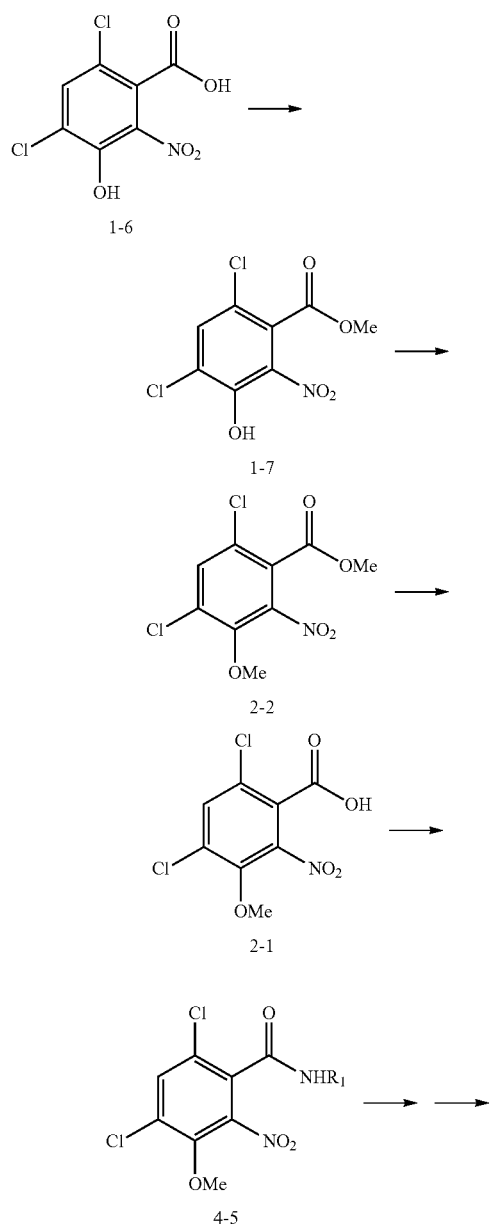

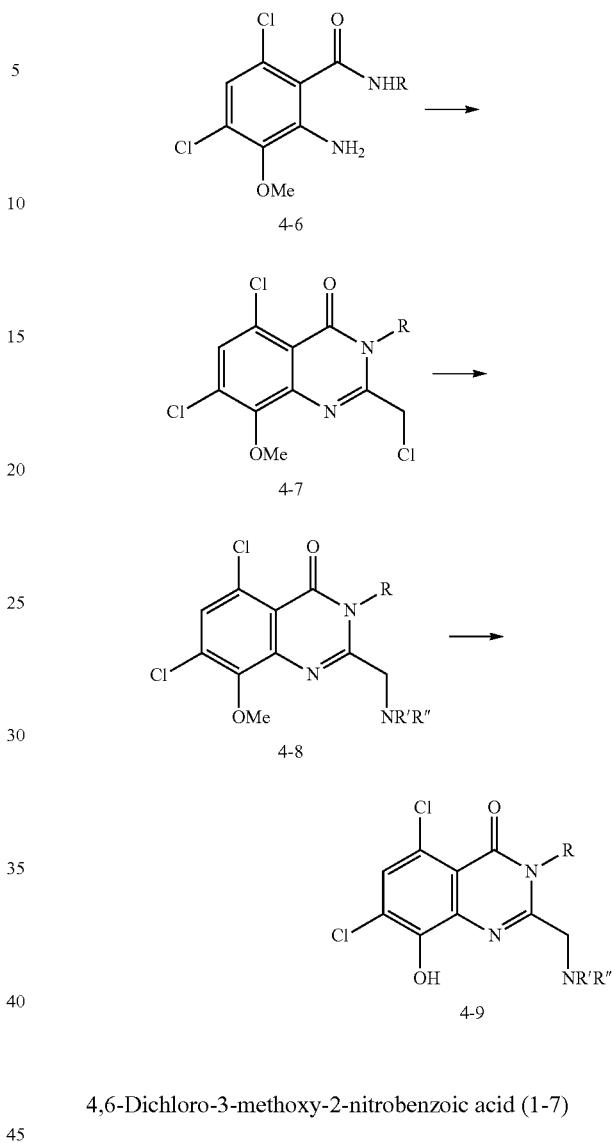

4,6-Dichloro-3-methoxy-2-nitrobenzoic acid (1-7)

To a solution of acid 1-6 (0.88 g, 3.5 mmol) in DMF (8 mL) was added $K_2CO_3$ (1.44 g, 10 mmol) followed by iodomethane (0.43 mL, 6.95 mmol). The reaction was heated to 60° C. for 17 h then DMF was removed under reduced pressure to give an orange gum. $H_2O$ (20 mL) was added and the solution was acidified to pH 1 with a 10% HCl solution. The aqueous solution was then extracted with EtOAc (30 mL) and washed with $H_2O$ and brine. After drying over $Na_2SO_4$ the reaction was filtered and concentrated to afford 1-7 as an orange gum (0.82 g, 88% yield). $^1H$ NMR (400 MHz, $CDCl_3$) δ 3.94 (s, 3H), 7.69 (s, 1H), 10.85 (br s, 1H).

Methyl 4,6-dichloro-3-methoxy-2-nitrobenzoate (2-2)

To the phenol 1-7 (10.4 g, 39.1 mmol) in HPLC grade acetone (150 mL) was added $K_2CO_3$ (15 g, 108.5 mmol) and iodomethane (5 mL, 80.3 mmol). The reaction was heated to 60° C. for 22 h. The flask was cooled and then $H_2O$ (40 mL) was added and the mixture stirred for 30 min. The volatiles were removed in vacuo and the residue was taken up in $CH_2Cl_2$ and $H_2O$. After extracting into $CH_2Cl_2$ (×3), the combined organic layers were washed with $H_2O$, dried over $Na_2SO_4$, filtered and concentrated to give the methyl ester 2-2 as an orange oil (9.92 g, 91% yield). $^1$H NMR (400 MHz, d6-DMSO) δ 0.95 (s, 3H), 8.22 (s, 1H).

4,6-Dichloro-3-methoxy-2-nitrobenzoic acid (2-1)

To the methyl ester 2-2 (9.90 g, 35.3 mmol) in MeOH (150 mL) was added 2N NaOH (150 mL) and the reaction was heated to reflux for 2.5 h. Methanol was removed in vacuo and the mixture was extracted with EtOAc. The aqueous layer was acidified to pH 2 with a concentrated solution of HCl and then extracted into EtOAc (×3). The combined organic layers were washed with brine, dried over $Na_2SO_4$, filtered and concentrated to provide the acid 2-1 as an orange solid (8.84 g, 94% yield). $^1$H NMR (400 MHz, d6-DMSO) δ 3.83 (s, 3H), 3.95 (s, 3H), 8.23 (s, 1H).

Preparation of F4095

4,6-Dichloro-3-methoxy-N-propyl-2-nitrobenzamide (4-5)

The acid 2-2 (1.41 g, 5.3 mmol) was heated to reflux in thionyl chloride (20 mL) for 2 h. After cooling, the volatiles were removed in vacuo and the residue was azeotroped with toluene. The resulting acid chloride was dried at high vacuum and then dissolved in anhydrous $CH_2Cl_2$ (50 mL), cooled to 0° C. then treated with propylamine (2.45 mL, 29.9 mmol). The reaction was warmed to room temperature for 2 h. The solvent was removed in vacuo and the residue was taken up in EtOAc and brine. The aqueous layer was extracted three times into EtOAc and the combined organic layers were washed with $H_2O$, dried over $Na_2SO_4$, filtered and concentrated to provide the amide in which R is propyl 4-5 as a light orange solid. (1.5 g, 92% yield). $^1$H NMR (400 MHz, d6-DMSO) δ 0.91 (t, J=7.0 Hz, 3H), 1.40 (q, J=7.0 Hz, 2H), 3.07 (q, J=7.0 Hz, 2H), 3.84 (s, 3H), 8.13 (s, 1H), 8.84 (br s, 1H).

4,6-Dichloro-3-methoxy-N-propyl-2-nitrobenzamide (4-6)

The nitro compound 4-5 in which R is propyl (1.50 g, 4.88 mmol) in glacial AcOH (50 mL) was heated to 80° C. with Fe powder (1.21 g, 21.7 mmol) for 1 h. The reaction was filtered through celite, washed with EtOAc (×3) and concentrated. The residue was diluted with EtOAc and sat. aq. $NaHCO_3$ and the aqueous layer was extracted with EtOAc (×3). The combined organic layers were washed with $H_2O$, dried over $Na_2SO_4$, filtered and concentrated to provide the amine 4-6 as a light brown oil (1.21 g, 89% yield). $^1$H NMR (400 MHz, d6-DMSO) δ 0.94 (t, J=7.2 Hz, 3H), 1.49 (q, J=7.2 Hz, 2H), 3.18 (q, J=7.2 Hz, 2H), 3.82 (s, 3H), 5.22 (br s, 2H), 6.77 (s, 1H), 8.42 (t, J=7.2 Hz, 1H).

5,7-Dichloro-2-(chloromethyl)-8-methoxy-3-propylquinazolin-4(3H)-one (4-7)

Amine 4-6 in which R is propyl (1.18 g, 4.26 mmol) in glacial AcOH (40 mL) was treated with chloroacetyl chloride (0.85 mL, 10.6 mmol) with or without the addition of concentrated sulfuric acid (0.6 eq) and the reaction was heated to reflux under $N_2$ for 4 h. Additional chloroacetyl chloride was added (0.85 mL) and the reaction was heated until no more starting material was observed by TLC. The reaction was cooled then the pH was adjusted to 5 using 2N NaOH. The reaction was extracted into $CH_2Cl_2$ (×3). The combined organic layers were dried over $Na_2SO_4$, filtered, concentrated and purified by flash chromatography eluting with 10% and then 15% EtOAc/petroleum ether 40°-60° C. to afford the chloromethyl compound 4-7 in which R is propyl as an oil (501 mg, 35% yield). $^1$H NMR (400 MHz, d6-DMSO) δ 0.95 (t, J=7.4 Hz, 3H), 1.64 (q, J=7.4 Hz, 2H), 3.97 (t, J=7.4 Hz, 2H), 3.99 (s, 3H), 4.91 (s, 2H), 7.77 (s, 1H).

5,7-Dichloro-2-((methylamino)methyl)-8-methoxy-3-propylquinazolin-4(3H)-one (4-8)

The chloromethyl compound 4-7 in which R is propyl (280 mg, 0.834 mmol) in anhydrous $CH_2Cl_2$ (8 mL) was cooled to 0° C. and methylamine solution in ethanol (2.0 mL, 33% wt) was added dropwise to the solution. The reaction was allowed to warm to room temperature overnight then volatiles were remove in vacuo. The residue was taken up in $CH_2Cl_2$ and sat. aq. $NaHCO_3$ then extracted with $CH_2Cl_2$ (×2). Combined organic layers were washed with $H_2O$, dried over $Na_2SO_4$, filtered and concentrated to afford the amine 4-8 in which R is propyl and R' and R" are hydrogen (220 mg, 80% yield) as an oil. $^1$H NMR (400 MHz, d6-DMSO) δ 0.95 (t, J=7.2 Hz, 3H), 1.62 (q, J=7.2 Hz, 3H), 2.36 (s, 3H), 3.80 (s, 2H), 3.98 (obscured triplet, J=7.2 Hz, 2H), 3.99 (s, 3H), 7.63 (s, 1H).

5,7-Dichloro-8-hydroxy-2-((methylamino)methyl)-3-propylquinazolin-4(3H)-one (F4095)

Methyl ether 4-8 (220 mg, 0.67 mmol) in $CH_2Cl_2$ (8 mL) was cooled to 0° C. and then $BBr_3$ (158 µL, 1.64 mmol) was added dropwise to the reaction. After warming to room temperature overnight the reaction was quenched carefully with MeOH at 0° C. The solution was concentrated and then methanol was added again. This procedure was repeated several times. NMR of the crude material revealed starting material (approx 15%) together with the desired product. The crude material was redissolved in anhydrous $CH_2Cl_2$ (8 mL) and treated dropwise with $BBr_3$ (200 mL). The reaction was warmed to room temperature overnight then the above work-up procedure was employed to give a the crude product. Trituration with MeOH (1 mL)/ether (20 mL) and filtration provided the desired target compound 1095 (158 mg, 57% yield). $^1$H NMR (400 MHz, d6-DMSO) δ 0.95 (t, J=7.2 Hz, 3H), 1.58 (q, J=7.2 Hz, 2H), 2.74 (s, 3H), 3.90 (t, J=7.2 Hz, 2H), 4.51 (s, 2H), 7.59 (s, 1H), 8.88 (s, 2H), 10.19 (s, 1H). MS m/z 316.2, 318.2 [M+H]$^+$.

TABLE 2

Compounds prepared according to Example 2 (Scheme 2)

| Compound | Structure | MW | ¹H NMR | Mass Spec |
|---|---|---|---|---|
| F4161 | 5,7-dichloro-8-hydroxy-3-methyl-2-((methylamino)methyl)quinazolin-4(3H)-one | Parent: 288.13 HBr Salt: | (400 MHz, d6-DMSO) δ 2.44 (s, 3H), 3.37 (s, 3H), 4.51 (t, J = 4.8 Hz, 2H), 7.60 (s, 1H), 8.99 (br s, 2H), 10.19 (s, 1H) | m/z 288.1, 290.1 [M + H]⁺ |
| F4473 | 5,7-dichloro-2-((diethylamino)methyl)-8-hydroxy-3-methylquinazolin-4(3H)-one | Parent: 330.21 HCl* Salt: 366.67 | ¹H NMR (400 MHz, d6-DMSO) δ 1.23 (m, 6H), 3.22 (s, 4H), 3.40 (s, 3H), 4.63 (s, 2H), 7.61 (s, 1H), 9.89 (bs, 1H), 10.65 (s, 1H) | m/z 330.1, 332.1 [M + H]⁺ |
| F4475 | 5,7-dichloro-8-hydroxy-3-methyl-2-(piperidin-1-ylmethyl)quinazolin-4(3H)-one | Parent: 342.23 HBr Salt: 423.13 | ¹H NMR (400 MHz, d6-DMSO) δ 1.40-1.90 (m, 6H), 3.18 (m, 2H), 3.40 (s, 3H), 3.57 (m, 2H), 4.70 (s, 2H), 7.61 (s, 1H), 9.09 (bs, 1H), 10.19 (s, 1H) | m/z 342.1, 344.1 [M + H]⁺ |
| F4477 | 5,7-dichloro-8-hydroxy-3-methyl-2-((propylamino)methyl)quinazolin-4(3H)-one | Parent: 316.19 HBr Salt: 397.1 | ¹H NMR (400 MHz, d6-DMSO) δ 0.97 (t, J = 7.9 Hz, 3H), 1.65 (m, 2H), 3.00 (m, 2H), 3.40 (s, 3H), 4.49 (s, 2H), 7.62 (s, 1H), 9.86 (bs, 1H), 10.24 (s, 1H) | m/z 316.0, 318.0 [M + H]⁺ |
| F4483 | 5,7-dichloro-3-ethyl-8-hydroxy-2-(piperidin-1-ylmethyl)quinazolin-4(3H)-one | Parent: 356.25 HBr Salt: 437.16 | ¹H NMR (400 MHz, d6-DMSO) δ 1.20 (t, J = 7.6 Hz, 3H), 1.40-1.90 (m, 6H), 3.17 (m, 2H), 3.56 (m, 2H), 3.88 (q, J = 7.6 Hz, 2H), 4.71 (s, 2H), 7.62 (s, 1H), 9.05 (bs, 1H), 10.23 (s, 1H) | m/z 356.3, 358.1 [M + H]⁺ |
| F4486 | 5,7-dichloro-3-ethyl-8-hydroxy-2-((methylamino)methyl)quinazolin-4(3H)-one HBr | Parent: 302.16 HBr Salt: 383.07 | ¹H NMR (400 MHz, d6-DMSO) δ 1.24 (t, J = 6.8 Hz, 3H), 2.76 (s, 3H), 3.94 (q, J = 6.8 Hz, 2H), 4.58 (s, 2H), 8.98 (br s, 2H), 10.25 (s, 1H). | m/z 302.2, 304.2 [M + H]⁺ |

TABLE 2-continued

Compounds prepared according to Example 2 (Scheme 2)

| Compound | Structure | MW | ¹H NMR | Mass Spec |
|---|---|---|---|---|
| F4487 | 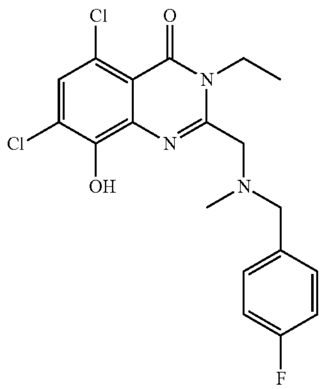 [SMILES: CCn1c(CN(C)Cc2ccc(F)cc2)nc2c(O)c(Cl)cc(Cl)c2c1=O] | Parent: 410.28 HBr Salt: 491.18 | ¹H NMR (400 MHz, d6-DMSO) δ 1.20 (t, J = 7.8 Hz, 3H), 2.93 (s, 3H), 3.88 (m, 2H), 4.55 (m, 2H), 4.76 (s, 2H), 7.23 (d, J = 7.5 Hz, 2H), 7.60 (d, J = 7.5 Hz, 2H), 7.65 (s, 1H), 8.79 (bs, 1H), 10.21 (s, 1H) | m/z 410.1, 412.2 [M + H]⁺ |
| F4492 | 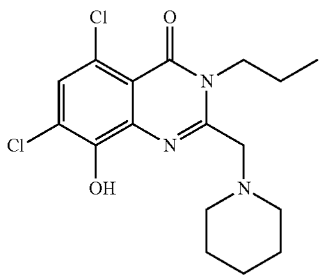 [SMILES: CCCn1c(CN2CCCCC2)nc2c(O)c(Cl)cc(Cl)c2c1=O] | Parent: 370.27 HBr Salt: 451.19 | ¹H NMR (400 MHz, d6-DMSO) δ 0.97 (t, J = 7.0 Hz, 3H), 1.43 (m, 1H), 1.61 (m, 2H), 1.75 (m, 1H), 1.86 (m, 4H), 3.22 (m, 2H), 3.59 (m, 2H), 3.85 (m, 2H), 4.78 (d, J = 4.0 Hz, 2H), 7.63 (s, 1H), 9.18 (br s, 1H), 10.25 (s, 1H). | m/z 370.1, 372.1 [M + H]⁺ |
| F4495 | 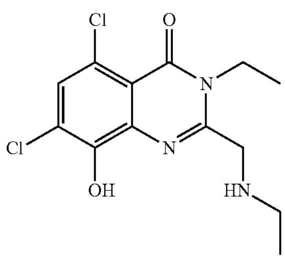 [SMILES: CCNCc1nc2c(O)c(Cl)cc(Cl)c2c(=O)n1CC] | Parent: 316.19 HBr Salt: 397.10 | ¹H NMR (400 MHz, d6-DMSO) δ 1.20 (t, J = 7.9 Hz, 3H), 1.31 (t, J = 7.9 Hz, 3H), 3.15 (m, 2H), 3.93 (m, 2H), 4.49 (s, 2H), 7.62 (s, 1H), 8.79 (s, 2H), 10.30 (s, 1H) | m/z 316.2, 318.2 [M + H]⁺ |
| F4496 | 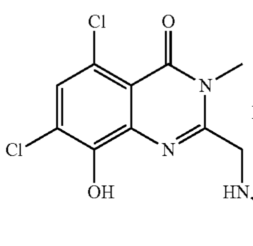 | Parent: 302.16 HBr Salt: 383.07 | ¹H NMR (400 MHz, d6-DMSO) δ 1.31 (t, J = 6.8 Hz, 3H), 3.14 (m, 2H), 3.44 (s, 3H), 4.54 (s, 2H), 7.65 (s, 1H), 8.95 (s, 2H), 10.30 (s, 1H). | m/z 302.2, 304.2 [M + H]⁺ |
| F4473 | 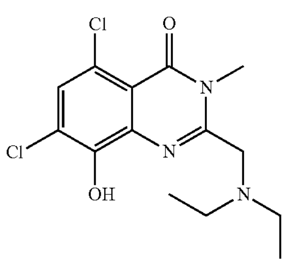 [SMILES: CCN(CC)Cc1nc2c(O)c(Cl)cc(Cl)c2c(=O)n1C] | Parent: 330.22 HBr Salt: 411.12 | ¹H NMR (400 MHz, d6-DMSO) δ 1.23 (m, 6H), 3.31 (m, 4H), 3.39 (s, 3H), 4.62 (s, 2H), 7.64 (s, 1H), 9.83 (bs, 1H), 10.65 (s, 1H). | m/z 330.1 [M + H]⁺, 332.1 |

TABLE 2-continued

Compounds prepared according to Example 2 (Scheme 2)

| Compound | Structure | MW | ¹H NMR | Mass Spec |
|---|---|---|---|---|
| F4551 | 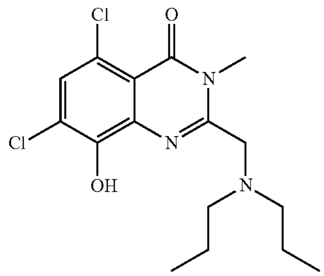 [SMILES: CCCN(CCC)Cc1nc2c(O)c(Cl)cc(Cl)c2c(=O)n1C] | Parent: 358.26 HBr Salt: 439.17 | ¹H NMR (400 MHz, d6-DMSO) δ 0.89 (m, 6H), 1.72 (m, 4H), 3.25 (m, 4H), 3.42 (s, 3H), 4.77 (s, 2H), 7.64 (s, 1H), 9.11 (bs, 1H), 10.40 (s, 1H). | m/z 358.1 [M + H]⁺, 360.1 |
| F4549 | 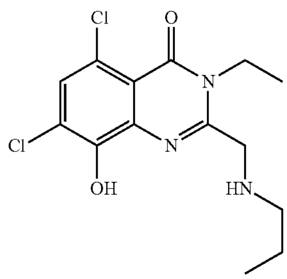 [SMILES: CCCNCc1nc2c(O)c(Cl)cc(Cl)c2c(=O)n1CC] | Parent: 330.21 HBr Salt: 411.12 | ¹H NMR (400 MHz, d6-DMSO) δ 0.95 (t, J = 7.6 Hz, 3H), 1.23 (t, J = 6.8 Hz, 3H), 1.74 (m, 2H), 3.06 (m, 2H), 3.96 (m, 2H), 4.56 (s, 2H), 7.65 (s, 1H), 8.94 (bs, 1H), 10.31 (s, 1H). | m/z 330.2 [M + H]⁺, 332.2 |
| F4550 | 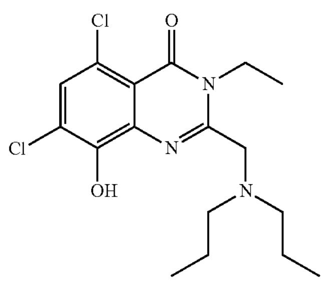 [SMILES: CCCN(CCC)Cc1nc2c(O)c(Cl)cc(Cl)c2c(=O)n1CC] | Parent: 372.30 HBr Salt: 453.20 | ¹H NMR (400 MHz, d6-DMSO) δ 0.88 (t, J = 7.2 Hz, 6H), 1.25 (m, 3H), 1.72 (m, 4H), 3.28 (m, 4H), 3.95 (d, J = 7.2 Hz, 2H), 4.78 (s, 2H), 7.67 (s, 1H), 9.16 (bs, 1H), 10.39 (s, 1H). | m/z 372.1 [M + H]⁺, 374.1 |
| F4530 | 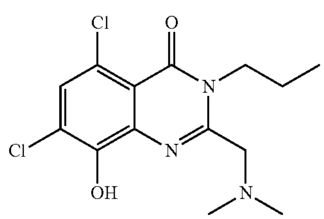 [SMILES: CCCn1c(CN(C)C)nc2c(O)c(Cl)cc(Cl)c2c1=O] | Parent: 330.21 HBr Salt: 411.12 | ¹H NMR (400 MHz, d6-DMSO) δ 0.95 (t, J = 6.8 Hz, 3H), 1.63 (m, 2H), 3.00 (3, 6H), 3.80 (m, 2H), 4.76 (s, 2H), 7.66 (s, 1H), 9.44 (bs, 1H), 10.23 (s, 1H). | m/z 328.3 [M + H]⁺, 330.3 |
| F4540 | 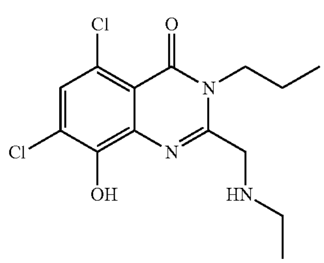 [SMILES: CCCn1c(CNCC)nc2c(O)c(Cl)cc(Cl)c2c1=O] | Parent: 330.21 HBr Salt: 411.12 | ¹H NMR (400 MHz, d6-DMSO) δ 0.94 (t, J = 6.8 Hz, 3H), 1.14 (t, J = 6.9 Hz, 3H), 1.49 (m, 2H), 3.17 (q, J = 6.8 Hz, 2H), 3.30 (m, 2H), 4.52 (s, 2H), 7.10 (s, 1H), 8.05 (br s, 1H), 8.18 (s, 1H). | m/z 330.3 [M + H]⁺, 332.3 |
| F4541 | 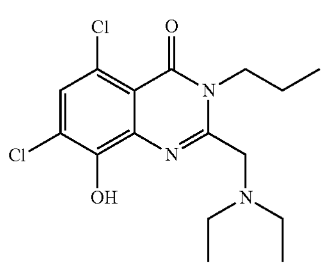 [SMILES: CCCn1c(CN(CC)CC)nc2c(O)c(Cl)cc(Cl)c2c1=O] | Parent: 357.26 HBr Salt: 439.17 | ¹H NMR (400 MHz, d6-DMSO) δ 0.95 (m, 3H), 1.28 (m, 6H), 1.64 (m, 2H), 3.33 (m, 4H), 3.86 (m, 2H), 4.71 (m, 2H), 7.67 (s, 1H), 9.14 (bs, 1H), 10.41 (s, 1H). | m/z 358.3 [M + H]⁺, 360.3 |

TABLE 2-continued

Compounds prepared according to Example 2 (Scheme 2)

| Compound | Structure | MW | ¹H NMR | Mass Spec |
| --- | --- | --- | --- | --- |
| F4542 | 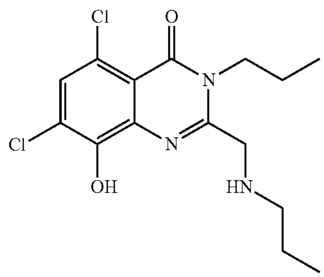 [SMILES: CCCNCc1nc2c(O)c(Cl)cc(Cl)c2c(=O)n1CCC] | Parent: 344.23 HBr Salt: 425.17 | ¹H NMR (400 MHz, d6-DMSO) δ 0.94 (m, 6H), 1.65 (m, 2H), 1.74 (m, 2H), 3.07 (m, 3H), 3.83 (m, 2H), 3.86 (m, 2H), 4.54 (s, 2H), 7.66 (s, 1H), 9.00 (s, 2H), 10.33 (s, 1H). | m/z 344.3 [M + H]⁺, 346.3 |
| F4543 | 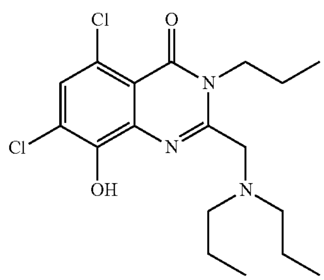 [SMILES: CCCN(CCC)Cc1nc2c(O)c(Cl)cc(Cl)c2c(=O)n1CCC] | Parent: 386.32 HBr Salt: 467.23 | ¹H NMR (400 MHz, d6-DMSO) δ 0.89 (t, J = 7.2 Hz, 3H), 0.94 (t, J = 7.2 Hz, 3H), 1.64 (q, J = 7.6 Hz, 2H), 1.71 (q, J = 7.6 Hz, 2H), 3.27 (m, 5H), 3.84 (t, J = 7.2 Hz, 2H), 4.76 (s, 1H), 4.78 (s, 1H), 7.66 (s, 1H), 9.14 (s, 2H), 10.39 (s, 1H). | m/z 386.1 [M + H]⁺, 388.1 |
| F4544 | 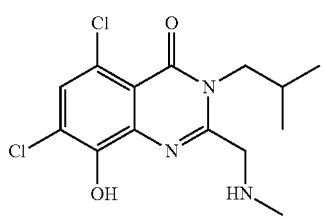 [SMILES: CNCc1nc2c(O)c(Cl)cc(Cl)c2c(=O)n1CC(C)C] | Parent: 330.22 HBr Salt: 411.12 | ¹H NMR (400 MHz, d6-DMSO) δ 0.91 (s, 6H), 2.07 (m, 1H), 2.75 (s, 3H), 3.79 (d, J = 6.0 Hz, 2H), 4.52 (s, 2H), 7.66 (s, 1H), 8.93 (s, 2H), 10.30 (s, 1H). | m/z 330.3 [M + H]⁺, 332.3 |
| F4545 | 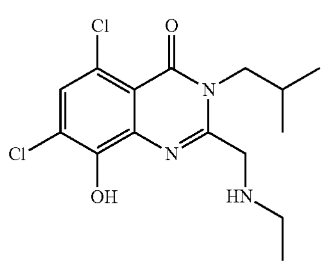 [SMILES: CCNCc1nc2c(O)c(Cl)cc(Cl)c2c(=O)n1CC(C)C] | Parent: 344.24 HBr Salt: 425.15 | ¹H NMR (400 MHz, d6-DMSO) δ 0.91 (s, 6H), 1.30 (t, J = 7.2 Hz, 3H), 2.07 (m, 1H), 3.18 (m, 2H), 3.81 (d, J = 7.6 Hz, 2H), 4.51 (s, 2H), 7.66 (s, 1H), 8.90 (s, 2H), 10.35 (s, 1H). | m/z 344.3 [M + H]⁺, 346.3 |
| F4546 | 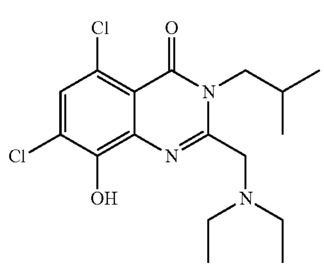 [SMILES: CCN(CC)Cc1nc2c(O)c(Cl)cc(Cl)c2c(=O)n1CC(C)C] | Parent: 372.29 HBr Salt: 453.20 | ¹H NMR (400 MHz, d6-DMSO) δ 0.91 (m, 6H), 1.28 (t, J = 6.8 Hz, 6H), 2.08 (m, 1H), 3.92 (m, 4H), 3.81 (d, J = 7.6 Hz, 2H), 4.70 (s, 1H), 4.71 (⁴J = 0.4 Hz, 1H), 7.66 (s, 1H), 9.11 (8, 2H), 10.40 (s, 1H). | m/z 372.3 [M + H]⁺, 374.3 |

TABLE 2-continued

Compounds prepared according to Example 2 (Scheme 2)

| Compound | Structure | MW | $^1$H NMR | Mass Spec |
| --- | --- | --- | --- | --- |
| F4547 | 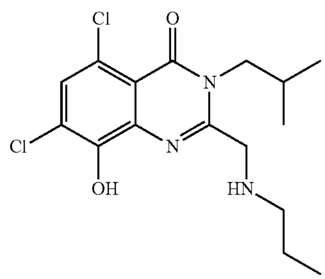 [SMILES: CCCNCc1nc2c(O)c(Cl)cc(Cl)c2c(=O)n1CC(C)C] | Parent: 358.27 HBr Salt: 439.18 | $^1$H NMR (400 MHz, d6-DMSO) δ 0.90 (m, 6H), 1.28 (t, J = 7.2, 3H), 1.74 (m, 2H), 2.06 (m, 1H), 3.06 (m, 2H), 3.81 (d, J = 8.0 Hz, 2H), 4.52 (s, 1H), 7.66 (s, 1H), 9.14 (s, 2H), 10.35 (s, 1H). | m/z 358.3 [M + H]$^+$, 360.3 |
| F4548 | 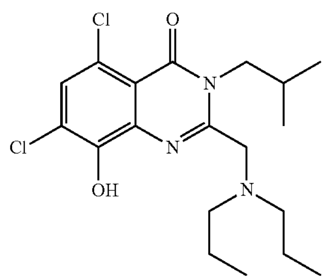 [SMILES: CCCN(CCC)Cc1nc2c(O)c(Cl)cc(Cl)c2c(=O)n1CC(C)C] | Parent: 400.35 HBr Salt: 481.25 | $^1$H NMR (400 MHz, d6-DMSO) δ 0.87-0.92 (m, 12H), 1.71 (m, 4H), 2.07 (m, 1H), 3.28 (m, 4H), 3.80 (d, J = 7.6 Hz, 2H), 4.75 ($^4$J = 4.4 Hz, 1H), 7.66 (s, 1H), 9.19 (s, 2H), 10.40 (s, 1H). | m/z 400.4 [M + H]$^+$, 402.4 |
| F4553 | 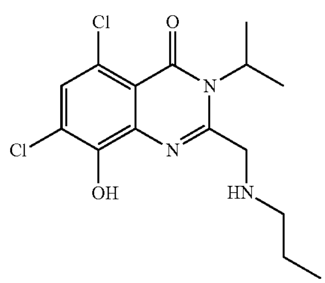 [SMILES: CCCNCc1nc2c(O)c(Cl)cc(Cl)c2c(=O)n1C(C)C] | Parent: 344.24 HBr Salt: 425.15 | $^1$H NMR (400 MHz, d6-DMSO) δ 0.95 (m, 3H), 1.58 (s, 3H), 1.59 (s, 3H), 1.65 (m, 2H), 3.11 (m, 2H), 4.43 (m, 1H), 4.71 (s, 2H), 7.62 (s, 1H), 8.99 (bs, 1H), 10.45 (s, 1H). | m/z 344.1 [M + H]$^+$, 346.1 |
| F4554 | 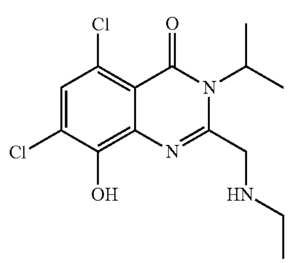 [SMILES: CCNCc1nc2c(O)c(Cl)cc(Cl)c2c(=O)n1C(C)C] | Parent: 330.21 HBr Salt: 411.12 | $^1$H NMR (400 MHz, d6-DMSO) δ 1.25 (m, 3H), 1.55 (s, 3H), 1.57 (s, 3H), 3.17 (m, 2H), 3.11 (m, 2H), 4.42 (m, 1H), 4.73 (s, 2H), 7.82 (s, 1H), 8.78 (bs, 1H), 10.30 (s, 1H). | m/z 330.3 [M + H]$^+$, 332.3 |
| F4555 | 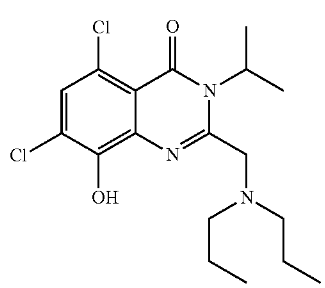 [SMILES: CCCN(CCC)Cc1nc2c(O)c(Cl)cc(Cl)c2c(=O)n1C(C)C] | Parent: 386.32 HBr Salt: 467.23 | $^1$H NMR (400 MHz, d6-DMSO) δ 0.93 (m, 6H), 1.57 (s, 3H), 1.58 (s, 3H), 1.74 (m, 4H), 3.17 (m, 4H), 3.11 (m, 2H), 4.35 (m, 1H), 4.76 (s, 2H), 7.67 (s, 1H), 8.90 (bs, 1H), 10.33 (s, 1H). | m/z 386.1 [M + H]$^+$, 388.1 |

TABLE 2-continued

Compounds prepared according to Example 2 (Scheme 2)

| Compound | Structure | MW | $^1$H NMR | Mass Spec |
|---|---|---|---|---|
| F4552 | 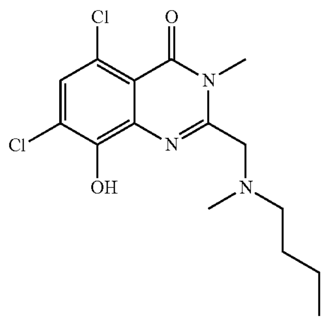 [SMILES: CCCCN(C)Cc1nc2c(O)c(Cl)cc(Cl)c2c(=O)n1C] | Parent: 344.24 HBr Salt: 425.15 | $^1$H NMR (400 MHz, d6-DMSO) δ 0.92 (t, J = 6.8 Hz, 3H), 1.32 (m, 2H), 1.74 (m, 2H), 2.98 (s, 3H), 3.31 (m, 2H), 3.39 (s, 3H), 4.68 (dd, $^2$J = 12.0, $^4$J = 5.6 Hz, 1H), 4.82 (d, $^2$J = 14.4 Hz, 1H), 7.66 (s, 1H), 9.26 (bs, 1H), 10.27 (s, 1H). | m/z 344.1 [M + H]$^+$, 346.1 |
| F4582 | 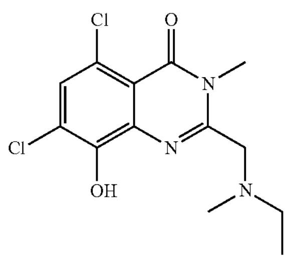 [SMILES: CCN(C)Cc1nc2c(O)c(Cl)cc(Cl)c2c(=O)n1C] | Parent: 316.18 HBr Salt: 397.10 | $^1$H NMR (400 MHz, d6-DMSO) δ 1.33 (t, J = 7.2 Hz, 3H), 2.96 (d, $^4$J = 4.4 Hz, 3H), 3.39 (m, 2H), 3.41 (s, 3H), 4.68 (dd, $^2$J = 16.8, $^4$J = 5.6 Hz, 1H), 4.82 (d, $^2$J =17.6 Hz, 1H), 7.66 (s, 1H), 9.25 (bs, 1H), 10.27 (s, 1H). | m/z 316.2, 318.2 [M + H]$^+$ |
| F4A | 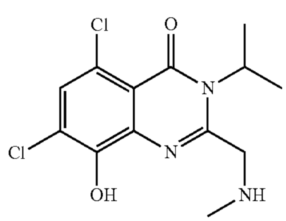 [SMILES: CNCc1nc2c(O)c(Cl)cc(Cl)c2c(=O)n1C(C)C] | Parent: 316.18 | | |
| F4B | 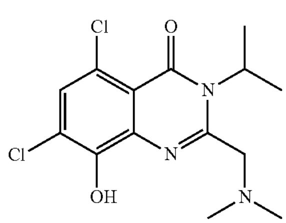 [SMILES: CC(C)n1c(CN(C)C)nc2c(O)c(Cl)cc(Cl)c2c1=O] | Parent: 320.21 | | |
| F4C | 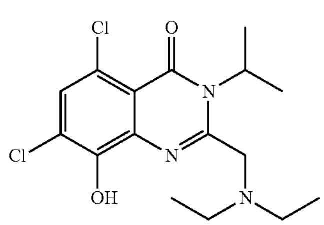 [SMILES: CCN(CC)Cc1nc2c(O)c(Cl)cc(Cl)c2c(=O)n1C(C)C] | Parent: 358.26 | | |

*Same method as for the other compounds. Final compound was neutralized with sat. aq. NaHCO$_3$ and converted to the HCl salt.

Example 3

Scheme 3
2,3-Disubstituted 8-hydroxy-3H-quinazolin-4-ones 4-9 can also be synthesised by the route depicted in Scheme 3. Thus, the methyl ester 2-2 (prepared according to Scheme 2 shown in Example 2) is reduced with iron powder in acetic acid to give aniline 2-3. Hydrolysis to the acid 2-4 then amide formation via the acid chloride affords 4-6. Dehydrative cyclisation is achieved by the action of refluxing chloroacetyl chloirde in acetic acid to afford chloromethyl intermediate 4-7. Amination, followed by deprotection with either BBr$_3$ or boiling hydrobromic acid generates the desired 2,3-disubstituted quinazolinone 4-9.

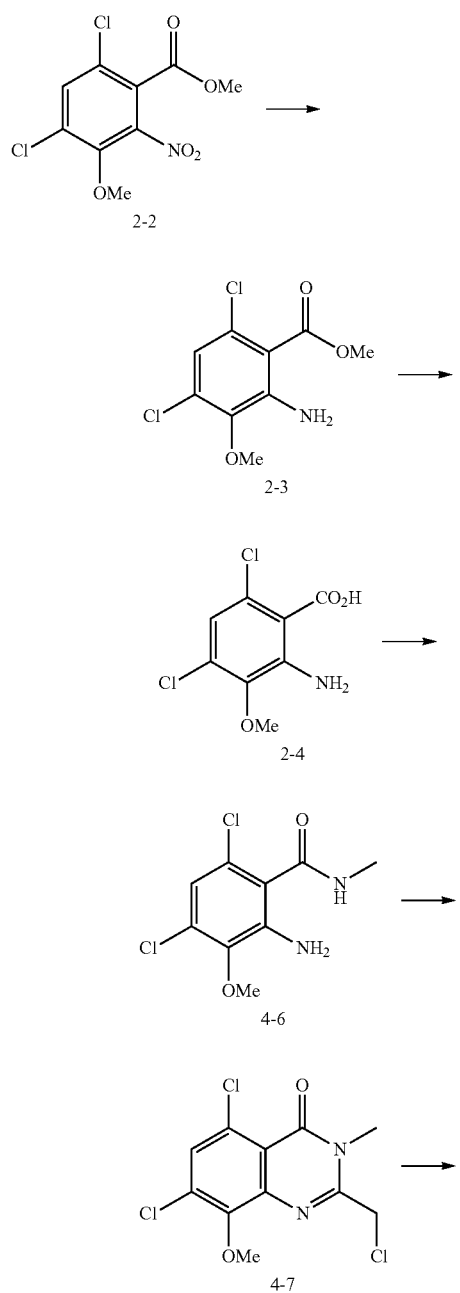

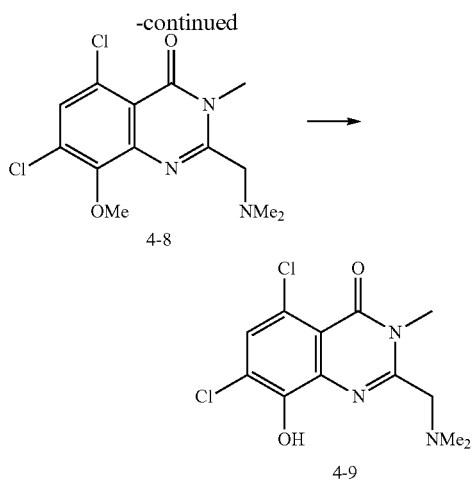

Methyl 2-amino-4,6-dichloro-3-methoxybenzoate (2-3)

Iron powder (18.2 g, 330 mmol) was added to a solution of methyl ester 2-2 (13.3 g, 480 mmol) in glacial acetic acid (120 mL). The mixture was stirred at 55° C. for 1.5 h and then filtered hot through celite, washing with ethyl acetate. The filtrate was concentrated then ethyl acetate and sat. aq. NaCO$_3$ were added. The organic layer was isolated, washed with H$_2$O, dried over K$_2$CO$_3$ and concentrated to give 2-3 as an off-white solid (11.6 g, 97% yield). $^1$H NMR (CDCl$_3$, 400 MHz) δ 3.79 (s, 3H), 3.89 (s, 3H), 6.71 (s, 1H).

2-Amino-4,6-dichloro-3-methoxybenzoic acid (2-4)

To a stirred solution of aniline 2-3 (11.5 g, 460 mmol) in methanol (250 mL) and H$_2$O (70 mL) was added 2N NaOH (25 mL). The reaction mixture was heated under reflux for 1 h, more 2N NaOH (25 mL) was added and the mixture was heated under reflux for a further 1 h. The solution was cooled and methanol was removed in vacuo. The mixture was dissolved in H$_2$O and extracted with ethyl acetate. The aqueous layer was acidified to pH 2 with conc. HCl. and then extracted into ethyl acetate (×3). The combined extracts were washed with brine, dried over Na$_2$SO$_4$, filtered and concentrated to provide the acid 2-4 as a beige solid (10.4 g, 95% yield). $^1$H NMR (MeOD, 400 MHz) δ 3.80 (s, 3H), 6.70 (s, 1H).

Preparation of F4269

2-Amino-4,6-dichloro-3-methoxy-N-methylbenzamide

To a mixture of the acid (3.13 g, 13.3 mmol) in toluene (22 mL) cooled to 0° C. was added thionyl chloride (3.9 mL, 53.0 mmol). The mixture was heated to reflux for 2 h and the resulting solution was concentrated to dryness. The acid chloride was dissolved in anhydrous CH$_2$Cl$_2$ (22 mL) and cooled to 0° C. Methylamine (15 mL, 8.0M solution in absolute ethanol, 120 mmol) was added and the reaction was allowed to warm to room temperature overnight. The mixture was concentrated and purified by flash chromatography eluting with 30%-60% ethyl acetate/petroleum ether 40-60° C. to provide the product as brown oil (2.43 g, 74% yield). $^1$H NMR (d6-DMSO, 400 MHz) δ 2.72 (t, J=4.0 Hz, 3H), 3.68 (s, 3H), 5.33 (s, 2H), 6.72 (s, 1H), 8.37 (d, J=4.0 Hz, 1H).

5,7-dichloro-2-(chloromethyl)-8-methoxy-3-methylquinazolin-4(3H)-one

To a solution of the amide (2.43 g, 9.76 mmol) in acetic acid (39 mL) was added chloroacetyl chloride (4.86 mL, 61 mmol) and the reaction was heated to reflux for 6 h then cooled to room temperature. The reaction was concentrated and then purified by flash chromatography eluting with 15%-40% ethyl acetate/petroleum ether 40-60° C. to provide the chloride as a solid (878 mg, 57% yield). $^1$H NMR (d6-DMSO, 400 MHz) δ 3.54 (s, 3H), 4.00 (s, 3H), 4.91 (s, 2H), 7.74 (s, 1H).

5,7-Dichloro-2-((dimethylamino)methyl)-8-methoxy-3methylquinazolin-4(3H)-one

To a solution of the chloromethyl compound (500 mg, 1.63 mmol) at 0° C. was added dimethylamine (12 mL, 2.0M, 24 mmol). The reaction was warmed to room temperature and stirred for 3 days and concentrated. The crude product was purified by flash chromatography eluting with 70%-80%-100% ethyl acetate/petroleum ether 40-60° C. to afford the amine as a yellow solid (391 mg, 76% yield). $^1$H NMR (d6-DMSO, 400 MHz) δ 2.26 (s, 6H), 3.56 (s, 2H), 3.58 (s, 3H), 3.97 (s, 3H), 7.68 (s, 1H).

5,7-Dichloro-2-(dimethylamino)methyl-8-hydroxy-3-methylquinazolin-4(3H)-one (PB1269)

To a mixture of the methoxy derivative (391 mg, 1.24 mmol) in anhydrous $CH_2Cl_2$ (6 mL) at 0° C. was added $BBr_3$ (234 mL, 2.48 mmol). The mixture was stirred at room temperature for 36 h after which it was cooled to 0° C. and the reaction was cautiously quenched with methanol. The solution was concentrated and then methanol was added again. This procedure was repeated several times. To the crude product was added ether and a few drops of methanol to precipitate F4269 as a cream solid that was collected by filtration and dried (340 mg, 72% yield).). δ $^1$H NMR (400 MHz, d6-DMSO) δ 2.95 (s, 3H), 2.96 (s, 3H), 3.33 (s, 3H), 4.67 (d, J=5.2 Hz, 2H), 7.62 (s, 1H), 9.37 (br s, 1H), 10.2 (s, 1H), m/z 315.1, 316.2 [M+H]$^+$ Example 4

Scheme 4
2,3-Disubstituted 8-hydroxy-3H-quinazolin-4-ones 4-9 can also be prepared by the route depicted in Scheme 4. Nitro acid 1-6 (prepared according to Scheme 1 shown in Example 1) was reduced to aniline 1-8 with iron powder and acetic acid. Acylation of 1-8 with chloroacetyl chloride provides the amide 1-9. One pot amide formation followed by dehydrative cyclisation to chloride 1-10 is achieved by the action of PCl$_3$ and an amine in refluxing toluene. After purification, amination of the chloromethyl compound 1-10 affords target compound F4271.

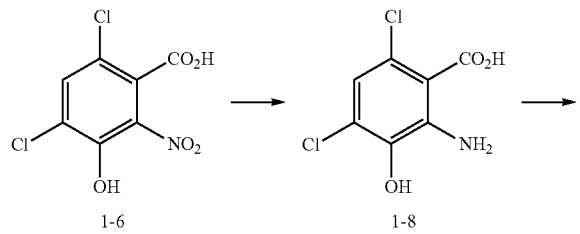

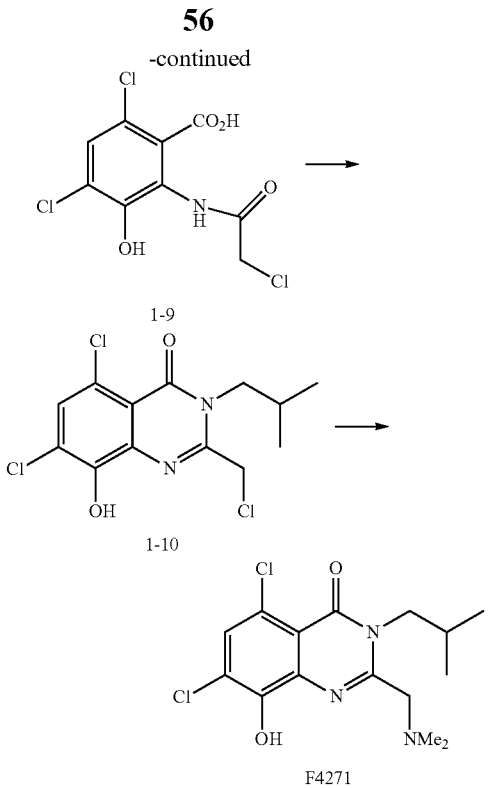

2-Amino-4,6-dichloro-3-hydroxybenzoic acid (1-8)

A mixture of 4,6-dichloro-3-hydroxy-2-nitrobenzoic 1-6 (700 mg, 2.78 mmol), Fe powder (400 mg, 7.16 mmol) and glacial acetic acid (13 mL) was heated at 80° C. for 50 min, cooled and the solids filtered off. The filtrate was concentrated to a brown solid. Purification by flash chromatography eluting with 1% AcOH/EtOAc to 3% AcOH/EtOAc afforded 2-amino-4,6-dichloro-3-hydroxybenzoic acid (1-8) as a light brown solid (582 mg, 94%). $^1$H NMR (d6-DMSO, 400 MHz) δ. 6.68 (s, 1H).

4,6-Dichloro-2-(2-chloroacetamido)-3-hydroxybenzoic acid (1-9)

To a mixture of the acid (1.0 g, 4.50 mmol) in anhydrous $CH_2Cl_2$ (22 mL) was added chloroacetyl chloride (1.4 mL, 18 mmol) at 0° C. The reaction was warmed to room temperature for 1 h and then concentrated to afford an orange oil. $^1$H NMR (d6-DMSO, 400 MHz) δ 4.18 (s, 2H), 7.56 (s, 1H), 9.83 (s, 1H), 10.22 (s, 1H).

5,7-Dichloro-2-(chloromethyl)-8-hydroxy-3-isobutylquinazolin-4(3H)-one

To a mixture of the acid (500 mg, 1.68 mmol) in anhydrous toluene (8 mL) was added PCl$_3$ (293 μL, 3.36 mmol) then isobutylamine (250 μt, 2.52 mmol). The reaction was heated to reflux for 2.5 h and then cooled to room temperature and concentrated. $H_2O$ was added followed by sat. aq. NaHCO$_3$ until the pH was 7. The mixture was extracted in EtOAc (×3) and the combined organic layers were washed with brine, dried over Na$_2$SO$_4$, filtered, concentrated and purified by flash chromatography eluting with 20% EtOAc/petroleum ether 40°-60° C. to provide the chloromethyl derivative (71 mg, 13% yield). $^1$H NMR (d6-DMSO, 400 MHz) δ 0.90 (d, J=6.8 Hz, 1H), 2.17 (m, 1H), 3.93 (d, J=7.6 Hz, 2H), 4.83 (s, 2H), 7.63 (s, 1H), 10.47 (s, 1H).

5,7-Dichloro-2-((dimethylamino)methyl)-8-hydroxy-3-isobutylquinazolin-4(3H)-one (F4271)

To a solution of the chloromethyl compound (50 mg, 0.149 mmol) in anhydrous $CH_2Cl_2$ (2 mL) at 0° C. was added dimethylamine (3 mL, 2.0M solution in MeOH, 6 mmol). The reaction was warmed to room temperature overnight then concentrated to dryness. The residue was taken up in MeOH (2 mL) and conc. HCl (0.5 mL) and then volatiles were removed in vacuo. Trituration with MeOH (few drops) and ether provided the desired amine (PB1271) as an off-white solid (19 mg, 33%). $^1$H NMR (400 MHz, d6-DMSO) δ 0.48 (m, 4H), 1.19 (t, J=4.80 Hz, 1H), 2.94 (s, 3H), 2.95 (s, 3H), 3.85 (d, J=6.8 Hz, 2H), 4.86 (d, J=4.80 Hz, 2H), 7.63 (s, 1H), 8.68 (br s, 1H), 10.64 (s, 1H), 10.65 (br s, 1H). MS m/z 344.3, 346.3 $[M+H]^+$.

Example 5

Assessment of Compounds of Formula I

The following Assays were used in the assessment of the compounds of formula I for suitability for use in the methods of the invention.

Assay 1. $H_2O_2$ Inhibition Assay.

This fluorescence assay evaluates the ability of a test compound to inhibit the generation of hydrogen peroxide ($H_2O_2$) by iron in the presence of a reducing substrate such as ascorbic acid. In the assay, iron in the form of $FeCl_3$ or copper is allowed to react with ascorbic acid by incubating for 1 hr at 37° C. in the presence of the fluorescing compound DCF and horseradish peroxidase. $H_2O_2$ generated by the system is assessed by measuring the specific fluorescence profile at the excitation and emission wavelengths of 485 and 530 nm respectively, in the presence of increasing concentrations of test compound. Test compounds are ranked according to their capacity to inhibit $H_2O_2$ generated by the system where lower values reflect greater ability to inhibit $H_2O_2$ production.

Assay 2 (a). Primary Neuronal Cells Neurotoxicity Assays

Cortical cultures were prepared as previously described (White et al., 1998). Embryonic day 14 BL6Jx129sv mouse cortices were removed, dissected free of meninges and dissociated in 0.025% (wt/vol) trypsin. Dissociated cells were plated in 48 well culture plates at a density of $2\times10^6$ cells/mL in MEM with 25% (vol/vol) FCS and 5% (vol/vol) HS and incubated at 37° C., 2 hrs. Media was then replaced with Neurobasal media (Invitrogen Life Technologies) and B27 supplements (Invitrogen Life Technologies). Cultures were maintained at 37° C. in 5% $CO_2$. Prior to experimentation, the culture medium was replaced with Neurobasal media and B27 minus antioxidants (Invitrogen Life Technologies).

Neuronal cortical cells were cultured for five days as per Assay 2 in NB media and B27 supplement.

On day six the test compounds were added to the neuronal cell cultures in NB media and B27 supplement minus antioxidants.

Test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 uM, 25 uM, 2.5 uM. Test compounds were not added directly to cells, instead they were added to a 48 well 'Drug Plate' as comprised below:

Preparation of "Drug Plate":
To a 48 well plate add:
Well 1: 576 ul NB+B27(no antioxidant)*+24 ul 2.5 uM test compound
Well 2: 576 ul NB+B27(no antioxidant)+24 ul 25 uM test compound
Well 3: 576 ul NB+B27(no antioxidant)+24 ul 250 uM test compound
Well 4: 576 ul NB+B27(no antioxidant)+24 ul 2.5 uM test compound
Well 5: 576 ul NB+B27(no antioxidant)+24 ul 25 uM test compound
Well 6: 576 ul NB+B27(no antioxidant)+24 ul 250 uM test compound
Well 7: 576 ul NB+B27(no antioxidant)+24 ul test compound diluent**
Well 8: 600 ul NB+B27(no antioxidant)

The Drug Plate was incubated at 37° C. for 15 mins. 200 ul of each well was added in triplicate to the corresponding cell plate. The cell plate was incubated at 37° C., for 4 days, (2 compounds are tested on each plate of cells).
*NB media and B27 (no antioxidants),
**PBT diluent 10% DMSO in NB+B27 (no antioxidants)

On completion of the assay, 1/10 volume MTS was added per well of plate (ie 25 ul/250 ul). The plates were incubated at 37° C. for 2 hrs, and then absorbance was read at 560 nm.

Assay 3. Metal Uptake Assay

M17 human neuroblastoma cells are plated out on 6 well plates and left overnight. Enough cells are added to give approximately 70% confluent the following day of the experiment. Test compounds are added to media and mixed with equi-molar amounts of CuCl2 solution. A=10 μM Cu+10 μM MPAC; B=10 μM Cu+10 μM MPAC.

Cells are incubated in 1 ml of media/MPAC/Cu mix for 5 hours at 37° C. At the end of the incubation the media is removed with a vacuum aspirator and 1 ml of PBS added to dislodge the cells. Cells are then put into Eppendorf tubes and pelleted. The PBS is removed and the remaining cell pellets are frozen at −20° C.

The cell pellets are prepared as follows:
Received cell pellets of similar levels in 1.5 ml microfuge tubes. Added 50 μl of concentrated Nitric Acid (Aristar, BDH) to each cell pellet and allowed them to digest over night. Heated the samples for 20 min at 90° C. to complete the digestion. The volume of each sample was reduced to ~45 ul after digestion. Added 1 ml of the 1% Nitric Acid diluent to each sample. (referred to as the "preparation solution" samples).

Measurements were made using a Varian UltraMass ICPMS instrument under operating conditions suitable for routine multi-element analysis.

The instrument was calibrated using Blank, 10, 50 and 100 ppb of a certified multi-element ICPMS standard solution (ICP-MS-CAI2-1, Accustandard) for Fe, Cu and Zn in 1% nitric acid. Used an certified internal standard solution containing 100 ppb Yttrium (Y 89) as an internal control (ICP-MS-IS-MIX1-1, Accustandard).

Assay 4. Physiochemical Properties
Polar Surface Area Calculations (PSA)
Polar surface area values were calculated using the web-based program available through "Molinspiration", a package for calculation of molecular properties.

Turbidimetric Solubility Measurements
The solubility estimate was measured at both pH 2.0 and pH 6.5. This is within the pH range that can be anticipated along the proximal gastrointestinal tract in humans.

The compounds are dissolved in DMSO to appropriate concentrations and then spiked into either 0.01 M HCl (approx. pH=2.0) or pH 6.5 isotonic phosphate buffer, the final DMSO concentration being 1%. Samples are then analysed via Nephelometry to determine a solubility range. [as per D. Bevan and R. S. Lloyd, Anal. Chem. 2000, 72, 1781-1787].

c Log P Values

Theoretical Log P values are determined using the ACD Log P software. The values quoted have been calculated from an untrained database and refer to the unionised species.

Assay 5. Pharmacokinetic Profile

The pharmacokinetic profile of test compounds is determined by the following assay:

Intravenous infusion of test compound; 2 mg/Kg in a suitable vehicle is administered to 2 rats and arterial blood is sampled up to 24 hours.

Oral administration of test compound; 30 mg/Kg in a suitable vehicle is administered via oral gavage to 2 rats and arterial blood is sampled up to 24 hours.

Plasma concentrations of test compound are determined by suitable analytical method.

Calculations:

$$CL_{total} = \frac{Dose_{IV}}{AUC_{IV}} \quad V_{d\beta} = \frac{CL_{total}}{\beta} \quad BA(\%) = \frac{AUC_{oral} * Dose_{IV}}{AUC_{IV} * Dose_{oral}}$$

$CL_{total}$=total plasma clearance after IV administration
$V_{d\beta}$=volume of distribution during the elimination phase after IV administration
BA=oral bioavailability
$AUC_{IV}$=area under the plasma concentration versus time profile from time zero to infinity after IV administration
$AUC_{oral}$=area under the plasma concentration versus time profile from time zero to infinity after oral administration
$\beta$=terminal elimination rate constant after IV administration Assay 6. Blood Brain Barrier Penetration Each compound tested demonstrates a permeability across a healthy BBB.

A bolus injection of each of the test compound (50 μL of a 3 mg/mL aqueous solution containing 40% propylene glycol and 10% ethanol) was administered by tail vein injection to male Swiss Outbred mice (5-7 weeks of age). Alternatively, test compound was orally administered to mice according to standard procedures known to the skilled person.

At 5 and 60 min post-dose (n=3 mice at each time point), blood was collected by cardiac puncture and the whole brain was removed by making an incision through the back of the skull. Mice were anaesthetized approximately 3-4 min prior to blood and brain harvest with an intraperitoneal injection of ketamine and xylazine (133 mg/kg and 10 mg/kg, respectively).

The whole brain was placed into pre-weighed polypropylene vials and stored at −20° C. until analysis. On the day of analysis, the whole brain was homogenised in 3 parts of water (on ice to reduce the potential for ex vivo brain degradation) and an aliquot of the brain homogenate and plasma was analysed for compound concentration by LCMS.

Standards were prepared by spiking blank brain homogenate and both samples and standards were processed by adding acetonitrile to the tissue homogenate, centrifuging and injecting an aliquot of the supernatant onto the LCMS.

To ensure complete recovery of compound from the brain, brain homogenate was spiked with compound (in 50% acetonitrile:50% water) to a nominal concentration of 500 ng/mL. The concentration of compound in the supernatant was then determined by LCMS and compared to the supernatant concentration when compound was added following precipitation with acetonitrile.

Calculations $$C_{brain} = C_{brain\ homogenate} - C_{brain\ vasculature}$$

$$C_{brain\ vasculature} = C_{plasma} * V_p$$

$$B{:}P = \frac{C_{brain}}{C_{plasma}} \quad P_{app}(cm/s) = \frac{C_{brain}}{\int_0^t C_{plasma} \cdot dt * A}$$

$C_{brain}$=concentration of compound in brain parenchyma (ng/g)
$C_{brain\ homogenate}$=concentration of compound in brain homogenate (ng/g)
$C_{brain\ vasculature}$=concentration of compound in brain vasculature (ng/g)
$C_{plasma}$=concentration of compound in plasma (ng/mL)
$V_p$=brain plasma volume (26 μl/g for male Swiss Outbred mice)
B:P=brain-to-plasma ratio
$P_{app}$=apparent permeability coefficient of compound permeating the blood-brain barrier
$\int_0^t C_{plasma} dt$=concentration of compound in plasma from time zero to 5 min post-dose (equivalent to the 5 min post-dose plasma concentration, assuming no back diffusion from brain to plasma within this time period)
A=surface area of capillaries forming the blood-brain barrier (240 cm²/g brain weight for mouse)

Assay 7

In Vitro Metabolism in Human Liver Microsomes

Incubation Methods:

The solubility of test compounds and their recovery from the incubation media were confirmed prior to the metabolic assay. Metabolic stability was performed by incubating test compounds individually (1 μM) at 37° C. with human liver microsomes. The metabolic reaction was initiated by the addition of a NADPH-regenerating system (i.e. NADPH is the cofactor required for CYP450-mediated metabolism) and quenched at various time points over the incubation period by the addition of acetonitrile. Additional samples with dual co-factors, i.e. NADPH and UDPGA (the co-factor for glucuronidation), were also included in the incubation for the qualitative assessment of the potential for glucuronide formation. The relative loss of parent compound and formation of metabolic products was monitored by LC/MS using a Waters/Micromass LCT mass spectrometer.

Calculations:

Test compound concentration versus time data were fitted to an exponential decay function to determine the first-order rate constant for substrate depletion. In cases where clear deviation from first-order kinetics was evident, only the initial linear portion of the profile was utilised to determine the degradation rate constant (k). Each substrate depletion rate constant was then used to calculate: [1] degradation half-life, [2] an in vitro intrinsic clearance value ($CL_{int,in\ vitro}$); [3] a predicted in vivo intrinsic clearance value ($CL_{int}$); and [4] a predicted in vivo hepatic extraction ratio ($E_H$).

$$t_{1/2} = \frac{\ln(2)}{k} \qquad [1]$$

$$CL_{int,\,in\,vitro} = \frac{k}{\text{microsomal protein content (0.4 mg protein/mL)}} \quad [2]$$

$$CL_{int} = CL_{int,\,in\,vitro} \times \frac{\text{liver mass (g)}}{\text{body weight (kg)}} \times \frac{45 \text{ mg microsomal protein}}{\text{g liver mass}} \quad [3]^*$$

$$E_H = \frac{CL_{blood}}{Q} = \frac{CL_{int}}{Q + CL_{int}} \quad [4]^*$$

The following scaling parameters were assumed for estimating metabolic stability parameters:

| Species | Liver mass (g liver/kg body mass) | Flow rate (Q) (mL/min/kg) |
|---|---|---|
| Human | 25.7 | 20.7 |

*45 mg microsomal protein/g liver mass was assumed

Predictions of In Vivo Hepatic Clearance and Hepatic Extraction Ratios:

The microsome-predicted hepatic extraction ratios ($E_H$) obtained based on the relative rate of degradation of the test compound in vitro, lead to test compounds being classified as low (<0.3), intermediate (0.3-0.7), high (0.7-0.95) or very high (>0.95) extraction compounds. The assumptions underlying this classification are stated below.

Note:

The use of hepatic microsomes in the prediction of the in vivo hepatic clearance and extraction ratio is based on a number of assumptions (Obach, 1999; Drug Metab. Dispos. 27: 1350-1359):

1) Hepatic (microsomal) metabolic clearance is the major clearance mechanism for compounds in vivo;
2) NADPH-dependent oxidative metabolism predominates over other metabolic routes (i.e. direct conjugative metabolism, reduction, hydrolysis, etc.); and,
3) Rates of metabolism and enzyme activities in vitro are truly reflective of those that exist in vivo.

Calculations of intrinsic clearance are based on the "in vitro $T_{1/2}$ method" (Obach, 1999), which has two further inherent assumptions:

1) The substrate concentration employed is well below the apparent $K_M$ for substrate turnover; and,
2) There is no significant product inhibition, nor is there any mechanism based inactivation of enzyme.

Data should be considered within these terms of reference.

CYP450 Isoform Inhibition

Fluorescence Based Assay

Microsomes containing individual recombinant human CYP450 enzymes (Supersomes™) were incubated in the presence of a fixed concentration of a probe substrate that forms a fluorescent metabolite upon CYP450-mediated metabolism. Varying concentrations of the test compound (i.e. potential inhibitor; 40-0.06 NM) were added to those incubations, and the $IC_{50}$ of test compound assessed according to the percent reduction in the extent of formation of the fluorescent metabolite as determined via analysis of the overall fluorescence response at a given wavelength for each isoform.

A known inhibitor of each CYP450 isoform was included in each assay as a positive control and its $IC_{50}$ was compared to literature values for acceptance of the assay.

The inherent fluorescence of the test compound was examined under the specific assay conditions for each isoform before and after the fluorometric assay to identify any compound-specific interference due to the parent compound or metabolic products. If the background fluorescence in these samples increased due to compound-specific interference, then the CYP450 inhibition samples were quantified using LC/MS assay. The positive control inhibitors were analysed by both methods (fluorescence and LC/MS detection) to confirm that the method of quantitation did not alter the $IC_{50}$ value.

CYP450 Isoform Inhibition Using a Specific Substrate Approach

The present study is a "Tier 2" screen to assess potential enzyme inhibition at a test compound concentration of 20 μM using a specific substrate approach in human liver microsomes.

The substrate specific enzyme inhibition study relies on the formation of a metabolite that is mediated by a specific CYP450 isoform using human liver microsomes. In the current study, the following reactions were monitored to assess interactions with specific CYP450 isoforms. A known inhibitor of each isoform was included in each assay as a positive control. The following $IC_{50}$ values have been reported in the literature using equivalent assay conditions for each CYP450 isoform:

| CYP450 isoform | Metabolic pathway | Positive control inhibitor | Literature $IC_{50}$ value |
|---|---|---|---|
| CYP1A2 | Phenacetin-O-deethylase | Furafylline | 1.76 [a] |
| CYP2C9 | diclofenac-4'-hydroxylation | Sulfaphenazole | 0.27 [a] |
| CYP2C19 | (S)-mephenytoin-4'hydroxylation | Ticlopidine | 2.7 [b] |
| CYP2D6 | dextromethorphan-O-demethylation | Quinidine | 0.058 [a] |
| CYP2E1 | Chlorzoxazone-6-hydroxylation | Tranylcypromine | 8.94 [a] |
| CYP3A4 * | midazolam-1'-hydroxylation | Ketoconazole | 0.019 [a] |
|  | testosterone-6β-hydroxylation |  | 0.026 [a] |

* Recommended that two structurally unrelated substrates be used for CYP3A4; Bjornsson et al. (2003) Drug. Metab. Dispos. 31: 815-832
[a] Walsky and Obach (2004) Drug. Metab. Dispos. 32: 647-660
[b] Turpeinen et al. (2004) Drug. Metab. Dispos. 32: 626-631

A single concentration (20 μM) of the test compound was incubated at 37° C. concomitantly with a specific substrate for an individual CYP isoform at ≤$K_m$, (i.e. phenacetin 50 μM, diclofenac 6 μM, (S)-mephenyloin 50 μM, dextromethorphan 3 μM, chlorzoxazone 20 μM, midazolam 2.5 μM and testosterone 50 μM) in human liver microsomes at a protein concentration of either 0.4 mg/mL (CYP1A2, CYP2C9, CYP2E1, CYP3A4 and CYP2D6) or 1.0 mg/mL (CYP2C19). The reaction was initiated by the addition of an NADPH-regenerating system and was quenched by the addition of acetonitrile prior to determining the concentration (and apparent rate of formation) of the specific metabolite by LC/MS.

The CYP450 inhibitory effect (i.e. % inhibition) of the test compound at a concentration of 20 μM was assessed according to the percent reduction in the apparent rate of formation of the specific metabolite, noting that the maximal metabolite formation occurs in the absence of inhibitor. Note that the $IC_{50}$ values for positive controls against each CYP450 isoform were estimated based on the % inhibition of CYP450 activity at two concentrations which bracketed the expected $IC_{50}$ value.

The $IC_{50}$ was deemed to be the concentration at which there was a 50% reduction in the amount of metabolite formed, relative to the maximal extent of formation.

TABLE 3
| | | Biological Data | | | | |
|---|---|---|---|---|---|---|
| | | In vitro Efficacy Profile | | | Physico-chemical properties | |
| | | $H_2O_2$ $IC_{50}$ ($\mu M$)[a] Fe-DA | | | | |
| | | % cf. Fe 0.4 µM/DA 50 µM | Cyctotox (% viable at 1 and 10 uM)[b] | Metal transport | Parent MW/ PSA | ClogP |
| F4271 | 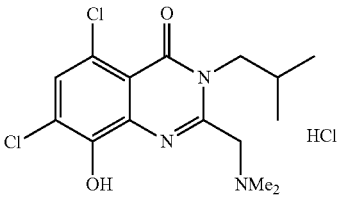 [SMILES: CC(C)Cn1c(CN(C)C)nc2c(O)c(Cl)cc(Cl)c2c1=O ; Cl] | 0.17 57% | M17 104.4, 61.5 102.3, 52.5 | Metal transport 27.8% | 344.34 HCl 380.70 | 3.17 |
| F4383 | 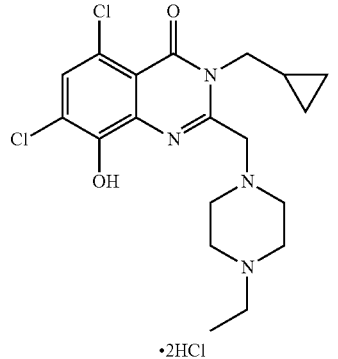 [SMILES: CCN1CCN(Cc2nc3c(O)c(Cl)cc(Cl)c3c(=O)n2CC2CC2)CC1] | 1.51 81% | M17: 118.5, 103.4 102.3, 92.7 | Metal transport 8% | 411.33 484.25 (2·HCl salt) | 3.57 |
| F4384 | 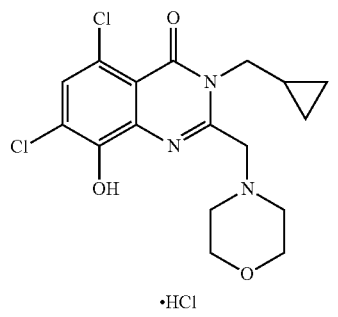 [SMILES: O=c1c2c(Cl)cc(Cl)c(O)c2nc(CN2CCOCC2)n1CC1CC1 ; Cl] | 2.15 59% | M17: 116.3, 86.5 106.4, 73.0 | Metal transport 17% | 384.27 420.73 (HCl salt) | 2.84 |
| F4385 | 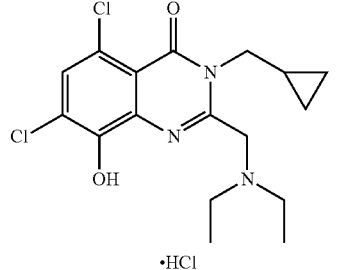 [SMILES: CCN(CC)Cc1nc2c(O)c(Cl)cc(Cl)c2c(=O)n1CC1CC1 ; Cl] | 0.91 86% | M17: 99.2, 97.7 105.0, 97.7 | Metal transport 9% | 370.28 406.74 (HCl salt) | 3.63 |

TABLE 3-continued

Biological Data

| | | In vitro Efficacy Profile | | | Physico-chemical properties | |
|---|---|---|---|---|---|---|
| | | $H_2O_2$ $IC_{50}$ (μM)[a] Fe-DA | | | | |
| | | % cf. Fe 0.4 μM/DA 50 μM | Cyctotox (% viable at 1 and 10 uM)[b] | Metal transport | Parent MW/ PSA | ClogP |
| F4386 | 5,7-dichloro-8-hydroxy-3-ethyl-2-((diethylamino)methyl)quinazolin-4(3H)-one ·HCl | 0.33 77% | M17: 101.8 105.2 99.8 91.9 101.4 111.7 107.9 106.8 | Metal transport 13% | 344.24 380.70 (HCl salt) | 3.18 |
| F4387 | 5,7-dichloro-8-hydroxy-3-(cyclopropylmethyl)-2-((N-methyl-N-propargylamino)methyl)quinazolin-4(3H)-one | 0.46 77% | M17: 104.0 19.8 92.7 20.7 95.9 35.5 100.7, 41.7 | Metal transport 111% | 366.24 402.7 (HCl salt) | 3.17 |
| F4391 | 5,7-dichloro-8-hydroxy-3-(cyclopropylmethyl)-2-(piperidin-1-ylmethyl)quinazolin-4(3H)-one | 0.59 97% (2 μM Fe) | M17: 87.4, 57.5 95.9, 70.5 96.0 66.5 | Metal transport 34% | 382.28 418.74 (HCl salt) | 3.88 |
| F4392 | 5,7-dichloro-8-hydroxy-3-ethyl-2-((N-methyl-N-propargylamino)methyl)quinazolin-4(3H)-one | 0.57 72% | | Metal transport 161% | 340.20 376.66 (HCl salt) | 2.73 |
| F4473 | 5,7-dichloro-8-hydroxy-3-methyl-2-((diethylamino)methyl)quinazolin-4(3H)-one ·HBr | 0.6 62% | 97.0 91.6 99.0 106.1 | Metal transport 9% | 330.22 HBr Salt 411.12 | 2.77 |

TABLE 3-continued
Biological Data
| | | In vitro Efficacy Profile | | | Physico-chemical properties | |
|---|---|---|---|---|---|---|
| | | $H_2O_2$ $IC_{50}$ (μM)[a] Fe-DA | | | | |
| | | % cf. Fe 0.4 μM/DA 50 μM | Cyctotox (% viable at 1 and 10 uM)[b] | Metal transport | Parent MW/ PSA | ClogP |
| F4475 | 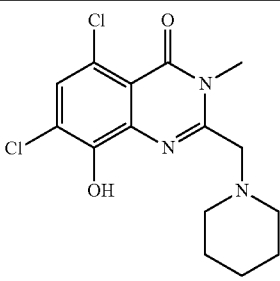 | 0.5 80% | | Metal transport 8% | 342.23 HBr Salt: 423.13 | 2.906 |
| F4477 | 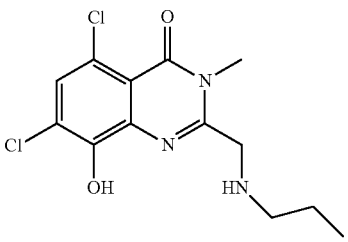 [SMILES: CCCNCc1nc2c(O)c(Cl)cc(Cl)c2c(=O)n1C] | 0.22 65% | | Metal transport 16% | 316.19 HBr Salt: 397.1 | 2.305 |
| F4480 | 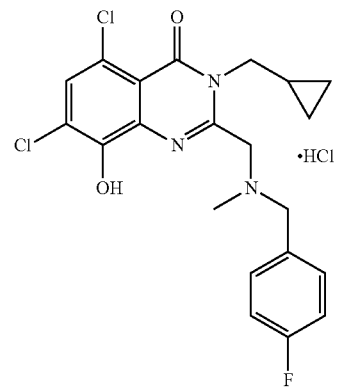 [SMILES: CN(Cc1ccc(F)cc1)Cc1nc2c(O)c(Cl)cc(Cl)c2c(=O)n1CC1CC1 ; Cl] | 0.47 46% | 91.6, 30.3 106.7, 33.3 | Metal transport 138% | 436.31 HCl: 472.77 | 4.60 |
| F4483 | 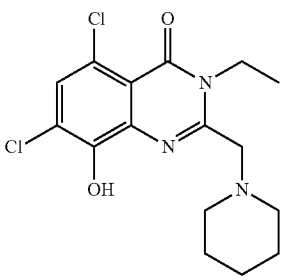 [SMILES: CCn1c(CN2CCCCC2)nc2c(O)c(Cl)cc(Cl)c2c1=O] | 0.33 62% | 93.4, 99.7 105.5, 72.3 | Metal transport 22% | 356.25 HBr salt: 437.16 | 3.44 |
| F4486 | 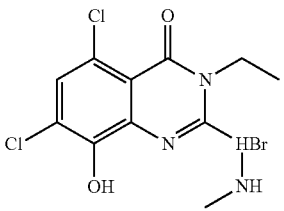 | 1.93 56% | 97.9, 52.2 101.4, 43.3 | Metal transport 14% | 302.16 HBr Salt: 383.07 | 1.776 |

TABLE 3-continued

Biological Data

| | In vitro Efficacy Profile | | | Physico-chemical properties | |
|---|---|---|---|---|---|
| | H₂O₂ IC$_{50}$ (μM)$^a$ Fe-DA | | | | |
| | % cf. Fe 0.4 μM/DA 50 μM | Cyctotox (% viable at 1 and 10 uM)$^b$ | Metal transport | Parent MW/ PSA | ClogP |
| F4487 | 0.76 53% | | Metal transport 133% | 410.2786 HBr Salt: 491.18 | |
| F4492 | 1.14 55% | | Metal transport 18% | 370.27 HBr Salt: 451.19 | 3.96 |
| F4495 | 0.77 45% | 89.3, 47.9 112.8, 57.1 | Metal transport 8% | 316.189 HBr Salt: 397.095 | 2.31 |
| F4496 | 0.83 45% | 102.7, 59.4 114.6, 101.2 | Metal transport 7% | 302.162 HBr Salt: 383.069 | 1.77 |
| F4499 | 1.89 55% | 99.1, 68.6 76.5, 78.1 | Metal transport 15% | 368.26 HCl salt: 404.72 | 3.32 |

TABLE 3-continued
| | Biological Data | | | | | |
|---|---|---|---|---|---|---|
| | | In vitro Efficacy Profile | | | Physico-chemical properties | |
| | | H$_2$O$_2$ IC$_{50}$ (μM)$^a$ Fe-DA | | | | |
| | | % cf. Fe 0.4 μM/DA 50 μM | Cyctotox (% viable at 1 and 10 uM)$^b$ | Metal transport | Parent MW/ PSA | ClogP |
| F4530 | 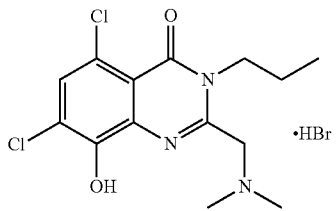 [SMILES: CCCn1c(CN(C)C)nc2c(O)c(Cl)cc(Cl)c2c1=O ; Br] | 0.29 57% | 105.0, 57.6. 96.2, 41.4. | Metal transport 24% | 409.00 HBr salt: 411.12 | 2.77 |
| F4535 | 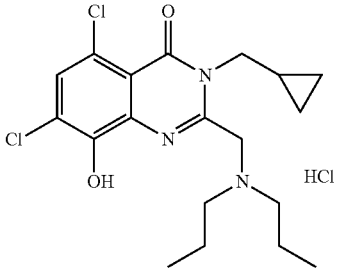 [SMILES: CCCN(CCC)Cc1nc2c(O)c(Cl)cc(Cl)c2c(=O)n1CC1CC1 ; Cl] | 0.88 62% | 87.0, 63.6. 103.0, 59.8. | Metal transport 25% | 410.34 HCl salt: 446.80 | 4.80 |
| F4536 | 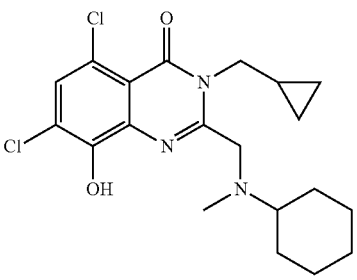 [SMILES: CN(Cc1nc2c(O)c(Cl)cc(Cl)c2c(=O)n1CC1CC1)C1CCCCC1] | 1.0 81% | 92.7, 64.9. 105.1, 91.9. 109.8, 40.9 | Metal transport 24% | 410.34 HCl salt: 446.80 | 4.72 |
| F4540 | 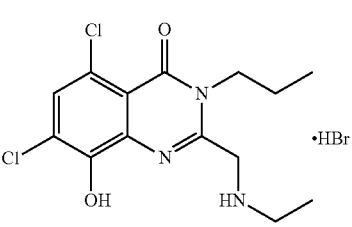 [SMILES: CCCn1c(CNCC)nc2c(O)c(Cl)cc(Cl)c2c1=O ; Br] | >10 122% | 100.4, 83.4. 111.5, 96.5 | Metal transport 14% | 330.21 HBr salt: 411.12 | 4.72 |
| F4541 | 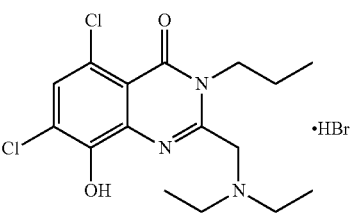 [SMILES: CCCn1c(CN(CC)CC)nc2c(O)c(Cl)cc(Cl)c2c1=O ; Br] | 0.74 107% | 97.3, 76.6. 96.4, 90.8. | Metal transport 13% | 357.26 HBr salt: 439.17 | 3.83 |

TABLE 3-continued

| | | Biological Data | | | | |
|---|---|---|---|---|---|---|
| | | In vitro Efficacy Profile | | | | |
| | | $H_2O_2$ $IC_{50}$ (μM)[a] Fe-DA | | | Physico-chemical properties | |
| | | % cf. Fe 0.4 μM/DA 50 μM | Cyctotox (% viable at 1 and 10 uM)[b] | Metal transport | Parent MW/ PSA | ClogP |
| F4542 | (structure) | 0.36 47% | 105.8, 36.6. 102.9, 73.4. 94.3, 48.7. | Metal transport 30% | 344.23 HBr salt: 425.14 | 3.36 |
| F4543 | (structure) | 0.50 71% | 92.0, 52.6. 107.4, 61.5. | Metal transport 62% | 386.32 HBr salt: 467.23 | 4.89 |
| F4544 | (structure) | 0.83 164% | 84.0, 29.7. 86.9, 26.7. | Metal transport 19% | 330.22 HBr salt: 411.12 | 2.70 |
| F4545 | (structure) | 0.43 148% | 86.4, 36.2. 85.0, 28.0. | Metal transport 40% | 344.23 HBr salt: 425.14 | 3.23 |
| F4546 | (structure) | 0.46 66% | 95.6, 63.7. 92.2, 86.5. 103.3, 100.3. | Metal transport 21% | 372.29 HBr salt: 453.20 | 4.23 |

TABLE 3-continued
| | Biological Data | | | | | |
|---|---|---|---|---|---|---|
| | | In vitro Efficacy Profile | | | | |
| | | $H_2O_2$ $IC_{50}$ (μM)$^a$ Fe-DA | | | Physico-chemical properties | |
| | | % cf. Fe 0.4 μM/DA 50 μM | Cyctotox (% viable at 1 and 10 uM)$^b$ | Metal transport | Parent MW/ PSA | ClogP |
| F4547 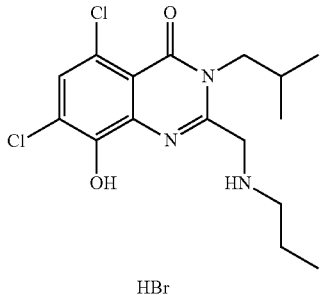 [SMILES: CCCNCc1nc2c(O)c(Cl)cc(Cl)c2c(=O)n1CC(C)C ; Br] HBr | | 0.50 34% | 75.0, 25.2. 83.9, 26.0. | Metal transport 54% | 358.27 HBr salt: 439.18 | 3.76 |
| F4548 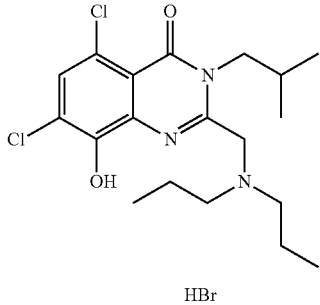 [SMILES: CCCN(CCC)Cc1nc2c(O)c(Cl)cc(Cl)c2c(=O)n1CC(C)C ; Br] HBr | | 0.38 40% | 96.5, 55.9. 96.0, 46.0. | Metal transport 38% | 400.35 HBr salt: 481.25 | 5.29 |
| F4549 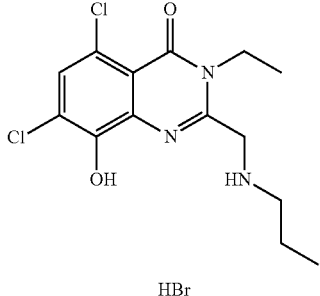 [SMILES: CCCNCc1nc2c(O)c(Cl)cc(Cl)c2c(=O)n1CC ; Br] HBr | | 0.30 40% | 98.5, 44.6. 99.7, 52.1. | Metal transport 22% | 330.21 HBr salt: 411.12 | 2.83 |
| F4550 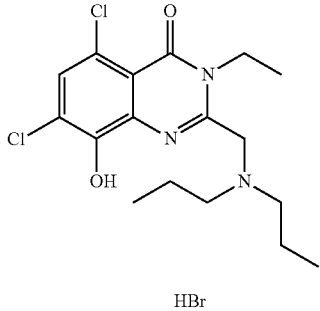 [SMILES: CCCN(CCC)Cc1nc2c(O)c(Cl)cc(Cl)c2c(=O)n1CC ; Br] HBr | | 0.75 128% | 88.7, 71.7. 94.7, 83.5 | Metal transport 35% | 372.30 HBr salt: 453.20 | 4.36 |

TABLE 3-continued

| | Biological Data | | | | |
|---|---|---|---|---|---|
| | | In vitro Efficacy Profile | | | |
| | | H₂O₂ IC₅₀ (μM)ᵃ Fe-DA | | Physico-chemical properties | |
| | | % cf. Fe 0.4 μM/DA 50 μM | Cyctotox (% viable at 1 and 10 uM)ᵇ | Metal transport | Parent MW/ PSA | ClogP |
| F4551 (5,7-dichloro-8-hydroxy-3-methyl-2-((dipropylamino)methyl)quinazolin-4(3H)-one · HBr) | | 0.45 56% | 89.7, 50.7. 96.9, 62.5. | Metal transport 30% | 358.26 HBr salt: 439.17 | 3.83 |
| F4552 (5,7-dichloro-8-hydroxy-3-methyl-2-((N-methyl-N-butylamino)methyl)quinazolin-4(3H)-one · HBr) | | 0.63 59% | 97.8, 58.7. 99.0, 62.8. | Metal transport 94% | 344.24 HBr salt: 425.15 | 3.30 |
| F4553 (5,7-dichloro-8-hydroxy-3-isopropyl-2-((propylamino)methyl)quinazolin-4(3H)-one · HBr) | | | | | 344.24 HBr salt: 425.15 | 3.14 |
| F4554 (5,7-dichloro-8-hydroxy-3-isopropyl-2-((ethylamino)methyl)quinazolin-4(3H)-one · HBr) | | | | | 330.21 HBr salt: 411.12 | 2.61 |

TABLE 3-continued

Biological Data

| Compound | Structure | In vitro Efficacy Profile $H_2O_2$ $IC_{50}$ (μM)[a] Fe-DA % cf. Fe 0.4 μM/DA 50 μM | Cyctotox (% viable at 1 and 10 uM)[b] | Metal transport | Parent MW/ PSA | ClogP |
|---|---|---|---|---|---|---|
| F4555 | 5,7-dichloro-8-hydroxy-3-isopropyl-2-((dipropylamino)methyl)quinazolin-4(3H)-one | | | | 386.32 HBr salt: 467.23 | |
| F4581 | 5,7-dichloro-3-(cyclopropylmethyl)-8-hydroxy-2-((N-methyl-N-ethylamino)methyl)quinazolin-4(3H)-one | 0.50 | | | 356.25 HBr salt: 392.71 | 3.22 |
| F4582 | 5,7-dichloro-8-hydroxy-3-methyl-2-((N-methyl-N-ethylamino)methyl)quinazolin-4(3H)-one | 0.55 | | | 316.19 HBr salt: 397.10 | 2.24 |

[a] concentration in μM of test compound required to inhibit 50% of $A_{beta}$ $H_2O_2$ production.
[b] % inhibition of $A_{beta}$ toxicity (average)

TABLE 4

Biological Data

| Compound | Bioavailability | | | | Druggability | | | |
|---|---|---|---|---|---|---|---|---|
| | Plasma Protein Binding (%)[a] | Mouse Plasma Conc. (ng/mL)[b] | Brain to Plasma Ratio (IV) (B:P)[c] | PK Studies in the Rat[d] | Metabolism (Predicted $E_H$)[e] | CYP450 Isoforms Study ($IC_{50}$)[f] | Equilibrium Solubility (pH2-7)[g] | Toxicity at 30 mg/Kg[h] |
| F4161 | Human 95.7 | Up to 510.4 | NA | $t_{1/2}$ = 6.7 h<br>Cmax = 6.7 μM<br>Tmax = 15 min<br>% dose in urine = 0.1<br>$AUC_{0-24\,h}$ = 846.6 μM/min<br>$I_{24}$ = 0.045-0.15 μM | Microsomes:<br>Human < 0.2<br>Hepatocytes:<br>Human = 0.20<br>Dog = 0.56<br>Rat = 0.29 | Analysis by LCMS:<br>CYP1A2 $IC_{50}$: 25.7 uM<br>CYP2C91 $IC_{50}$: >40 uM<br>CYP2C19 $IC_{50}$: >40 uM<br>CYP2D6 $IC_{50}$: >40 uM<br>(substrate specific approach) | 196 μg/mL - 746 μg/mL - pH dependent | Not toxic |

TABLE 4-continued

| | Bioavailability | | | | Druggability | | | |
|---|---|---|---|---|---|---|---|---|
| Compound | Plasma Protein Binding (%)[a] | Mouse Plasma Conc. (ng/mL)[b] | Brain to Plasma Ratio (IV) (B:P)[c] | PK Studies in the Rat[d] | Metabolism (Predicted $E_H$)[e] | CYP450 Isoforms Study ($IC_{50}$)[f] | Equilibrium Solubility (pH2-7)[g] | Toxicity at 30 mg/Kg[h] |
| F4267 | Human 99.5 | Up to 1166.6 | 3.46 at 5 min 2.02 at 60 min | Enterohepatic recycling $t_{1/2}$ = 4.9 h (oral dosing only-30 mg/Kg) $I_{24}$ = 0.25-0.5 uM | Microsomes: Human < 0.31 Hepatocytes: Human = 0.44 Dog = 0.39 Rat = 0.45 | Substrate Specific: CYP1A2 $IC_{50}$: 15.3 uM CYP2C9 $IC_{50}$: >30 uM CYP2C19 $IC_{50}$: >30 uM CYP2D6 $IC_{50}$: 7.4 uM CYP3A4 $IC_{50}$: 13.8 uM CYP3A4 $IC_{50}$: >30 uM | 393-1705 µg/mL - pH dependent | Not toxic |
| F4268 | Mouse 79.9-82.2 Rat 94.5-94.8 Human 97.1 | Up to 975.9 | 2.96 at 5 min 2.63 at 60 min | Enterohepatic recycling $t_{1/2}$ = 4.3 h (oral-30 mg/Kg) Cmax = 10 uM Tmax = 20 min Rel. Exposure: 51.9% 0.1% dose in urine $I_{24}$ = 0.02-0.05 uM | Microsomes: Human < 0.2 Hepatocytes: Human = 0.28 Dog = 0.49 Rat = 0.30 | Substrate specific: CYP1A2 IC50: ~20 uM CYP2C9 $IC_{50}$: >20.0 uM CYP2C19 $IC_{50}$: >20.0 uM CYP2D6 $IC_{50}$: >20 uM CYP2E1 $IC_{50}$: >20 uM CYP3A4-Midazolam $IC_{50}$: ~20 uM CYP3A4-Testosterone $IC_{50}$: >20 uM | 3814-10184 µg/mL - not pH dependent | Not toxic |
| F4269 | Mouse 32.2-41.8 Rat 88.4-92.6 Human 94.1-94.6 | Up to 492.1 | 2.96 at 5 min 2.12 at 60 min | Enterohepatic recycling $t_{1/2}$ = 5.6 h (oral-20 mg/Kg) Cmax = 3.3 uM Tmax = 22.5 min $AUC_{0-24\,h}$ (min*umol/L) = 330.29 0.1% dose in urine $I_{24}$ = 0.01-0.03 uM | Microsomes: Human < 0.2 Hepatocytes: Human = 0.38 Dog = 0.54 Rat = 0.35 | Substrate specific: CYP1A2 24.1 uM CYP2C9 >30 uM CYP2C19 >30 uM CYP2D6 >30 uM CYP3A4-Midazolam >30 uM CYP3A4-Testosterone >30 uM | 166-2670 µg/mL - pH dependent | Not toxic |
| F4385 | Human 98.7-99.2 | Up to 9074 | Oral dosing: 0.31 at 30 min, 0.42 at 240 min | Enterohepatic recycling $t_{1/2}$ = 14.7 h (oral-20 mg/Kg) Cmax = 7.3 uM Tmax = 30 min $AUC_{0-24\,h}$ (min*umol/L) = 3124.7 0.05% dose in urine $I_{24}$ = 0.5-1.5 u | Microsomes: Human < 0.2 Hepatocytes: Human = 0.55 Dog = 0.37 Rat = 0.35 | Substrate specific: CYP1A2 13.4 uM CYP2C9 >30 uM CYP2C19 >30 uM CYP2D6 5.1 uM CYP3A4-Midazolam 21.5 uM CYP3A4-Testosterone >30 uM | 683-1662 µg/mL - pH dependent | Not toxic |
| F4386 | NA | Up to 3294.1 | NA | NA | NA | NA | NA | Not toxic |
| F4387 | NA | Up to 942.7 | 0.65 at 5 min 0.29 at 60 min | NA | Microsomes: Human = 0.75 | NA | NA | Not toxic |

TABLE 4-continued

Biological Data

| Compound | Bioavailability | | | | Druggability | | | |
|---|---|---|---|---|---|---|---|---|
| | Plasma Protein Binding (%)[a] | Mouse Plasma Conc. (ng/mL)[b] | Brain to Plasma Ratio (IV) (B:P)[c] | PK Studies in the Rat[d] | Metabolism (Predicted $E_H$)[e] | CYP450 Isoforms Study ($IC_{50}$)[f] | Equilibrium Solubility (pH2-7)[g] | Toxicity at 30 mg/Kg[h] |
| F4391 | NA | Up to 17255.9 | NA | NA | NA | NA | NA | Not toxic |
| F4473 | NA | Up to 1356.2 | NA | NA | NA | NA | NA | Not toxic |
| F4483 | NA | Up to 1585.2 | NA | NA | NA | NA | NA | Not toxic |
| F4486 | NA | Up to 1115 | Oral dosing: 0.23 at 30 min, 0.22 at 240 min | NA | NA | NA | NA | Not toxic |
| F4495 | Human 97.7-97.6 | Up to 8935 | Oral dosing: 0.65 at 30 min, 0.64 at 240 min | Enterohepatic recycling $t_{1/2}$ = 4.1 h (oral-20 mg/Kg) Cmax = 56.7 uM Tmax = 30 min $AUC_{0-24h}$ (min*umol/L) = 5218.4 0.18% dose in urine $I_{24}$ = 0.05-0.3 uM | Microsomes: Human < 0.2 Hepatocytes: Human = 0.22 Dog = 0.56 Rat = 0.35 | Substrate specific: CYP1A2 13.7 uM CYP2C9 >30 uM CYP2C19 >30 uM CYP2D6 9.5 uM CYP3A4-Midazolam >30 uM CYP3A4-Testosterone >30 uM | 2227-4727 μg/mL - not pH dependent | Not toxic |
| F4496 | Human 91.8-93.1 | Up to 3330.8 | Oral dosing: 1.42 at 30 min, 1.97 at 240 min | Enterohepatic recycling $t_{1/2}$ = 6.1 h (oral-20 mg/Kg) Cmax = 7.61 uM Tmax = 45 min $AUC_{0-24h}$ (min*umol/L) = 1069.3 0.19% dose in urine $I_{24}$ = 0.02-0.1 uM | Microsomes: Human < 0.2 Hepatocytes: Human = 0.43 Dog = 0.66 Rat = 0.35 | Substrate specific: CYP1A2 22 uM CYP2C9 >30 uM CYP2C19 >30 uM CYP3A4-Midazolam: 4.4 uM CYP3A4-Testosterone 8.6 uM | 224-1504 μg/mL - not pH dependent | Not toxic |

Example 6

Parkinson's Disease In Vivo Technique: 6-OHDA Model

Preparation of the toxin 6-OHDA (1.65 mg/mL, Sigma Cat# H-4381):

6-OHDA toxin is dissolved in ascorbic acid solution (0.2 mg/mL in $dH_2O$), store in dark on ice. To increase the speed of anaesthesia and reduce stress to the mouse, there is pre-medication with atropine (0.5 mg/kg) and xylazine (10 mg/kg) is injected subcutaneously via a 27 gauge needle).

To Prepare the Lesion Needle to Inject 6-OHDA:

PBS is sucked up into the line (ensure no air bubbles) with up to 200 ml in a Hamilton syringe. Syringe is placed the in the Kd Scientific syringe pump and secured. Pump is turned the on and syringe is loaded into the pump. Pump volume is set at 2 ml and the rate is set at 0.5 ml/min. The lesion needle is positioned so that the bevelled (eye) of the needle is at a 45° angle from the midline and tightened to secure the needle. Pump is run and checked for fluid coming out.

Anaesthesia 3-4% isoflurane is carried by oxygen to induce anaesthesia and 1-2% for maintenance of anaesthesia. Animal is placed in small induction chamber and subjected to a few minutes of 4% isoflurane in oxygen at a flow rate of approx 1 l/min. Mouse is then placed in stereotaxic frame. The anaesthetic tube is disconnected from induction box and isoflurane reduced to 2% conc and oxygen flow rate to approx 300-400 cm/min. Tube is connected to the nose piece attached to stereotaxic frame so that anaesthetic gas can be constantly administered during surgery. LHS ear bar is screwed at approx 3 mm. RHS ear bar is screwed in until there is no sideways head movement (about 5 mm). Front incisors are placed over the mouthguard and put nose-guard on (3 mm below 0). Mouthguard is screwed into place and ensured the top of the mouse's head is level (re-check this once the animal's skull is exposed).

Using a scalpel (size 4, blade 22), the scalp is cut down the centreline of the mouse's head to expose the skull. Typically 10-15 mm. The surface of the skull is dried with a cotton bud. Drill hole is measured with a ruler 3 mm posterior from Bregma and between 1 and 1.5 mm laterally from the centre line. The skull is drilled into this position until the surface of the brain is exposed.

Toxin Loading

6-OHDA is sucked up to fill approximately 15 cm of the line and the syringe. Fluid is ensured to be coming out of needle. The bevelled of the needle is aligned over the centre-line where Bregma crosses, viewed by Motik dissecting microscope. The needle is ensured to be a few mm above the skull before positioning. Frame is moved 2.9 mm in a posterior direction and 1.1 mm (11 small notches) laterally to the right (for RHS injections) from the starting coordinates at Bregma. Needle is moved down until the tip of the needle just touches the surface of the brain.

Needle is lowered to the required depth of 4.6 mm and brain is allowed to settle for 2 min.

2 ml of toxin is injected into the RHS SNpc, taking 4 min. 2 min is allowed to ensure the toxin disperses. Needle is withdrawn and antiseptic applied to the wound, with suture or superglue to close.

Mouse is wrapped in a piece of tissue and placed in a warm recovery box (on a heat pad) with water bottles (50 ml tubes) warmed to 50° C. Panadol® syrup is added to mouse's water bottle.

Rotation Method

Rotation is recorded by the Computer based Rotacount system—(Columbus Instruments, Columbus, Ohio, USA). The system comprised of 8 bowls with sensors connected to a computer which measures incremental turns (90 degrees and full turns 360 degrees) either clockwise or counter clockwise. The sensors are positioned above the centre of each bowl about 30 cm above each. Tubing and a thin empty plastic pipette are attached so that the sensor is now extended to with a few cm of the base of the bowl.

Mice are placed individually into the eight bowls. Mice are secured to the pipettes via a cable tie and tape. A cable tie (at least 15 cm in length) is looped around the mouse's body (upper chest, behind front legs) and tightened to give a secure but not too tight hold ensuring that the end is upright. Once tied mice are returned to their bowls for two minutes. Once the mice are secure, the loose ends of the cable tie can be taped to the bottom of the pipette. This now means that any movement by the mouse will register on the sensor. Once all mice are secure it is then possible to start the software. Data is recorded in 5 min bins. The mice are left alone in the behaviour room for 30 mins to acclimatise to their surroundings. This also gives baseline data for each animal.

To set up the amphetamine syringes, amphetamine (Sigma) is weighed out using SOP G8. Typically 5 mg in 4 ml of saline is enough for 12-15 mice in a day. Amphetamine is injected ip at a dose of 5 mg/kg. To aid uptake of the amphetamine, a further 300 ml of saline is taken up into each syringe.

Once the 30 mins has elapsed, mice are injected. Once the mice have all been injected, their movements are monitored for two mins as the amphetamine takes effect. The mice are left for 60 min as the computer records the rotations. The experiment can be stopped any time after 60 mins. Rotations are recorded as CW-clockwise or CCW counter clockwise Inclusion/Exclusion Criteria Day 3:

The animal is included if the total rotations in the 60 min post amphetamine is greater than 200 and less than 450.

The animal is excluded if less than 200 rotations are recorded in the 60 mins and is no longer included in the trial. Animals failing to reach the selection criteria are culled.

TABLE 5

6-OHDA lesion data

| Treatment - control or compound | Behaviour (Rotation)% SSV (total turns/ h ± SD) | SN cell counts % of SSV (SSV = 0%) (cells ± SD) | Mice in trial (n=)/ mice in expt |
|---|---|---|---|
| Unlesioned mice | ND | 284.73% (6184 ± 197.07) | 6 |
| SSV Control | 0% (259.05 ± 120.21) | 0% (1920.56 ± 641.47) | 10/26 |
| F4076 | 16.54% (216.22 ± 86.46) | 129.77% (4412.80 ± 502.55) | 9/10 |
| F4267 (30 mg kg) | 36.33% (164.93 ± 110.90) | 110.44% (4041.70 ± 799.55) | 9/15 |
| F4267 (15 mg kg) | −23.39% (319.67 ± 171.05) | 77.86% (3415.96 ± 498.05) | 8/10 |
| F4267 (5 mg kg) | 7.01% (240.89 ± 171.99) | 55.79% (2992.00 ± 883.84) | 7/9 |
| F4268 | 56.04% (114.56 ± 71.86) | 93.96% (3725.04 ± 842.65) | 9/12 |
| F4269 | 48.85% (132.50 ± 81.93) | 68.91% (3243.93 ± 724.98) | 8/12 |
| F4385 | 49.98% (129.57 ± 16.26) | 56.81% (3011.56 ± 502.27) | 9/17 |
| F4387 | 24.51% (195.57 ± 114.48) | 46.90% (2821.24 ± 940.22) | 7/12 |
| F4495 | 18.06% (212.29 ± 101.41) | 57.22% (3019.56 ± 318.79) | 8/27 |
| F4496 | 36.62% (164.20 ± 100.40) | 95.68% (3758.11 ± 510.98) | 10/27 |
| L-DOPA | 52.26% (123.67 ± 80.90) | 1.73% (1953.78 ± 280.21) | 6/9 |
| Selegiline | 71.13% (74.80 ± 57.95) | 0.43% (1928.89 ± 301.77) | 6/9 |

Example 7

Parkinson's Disease In Vivo Technique: MPTP

MPTP (1-methyl 4-phenyl 1,2,3,6-tetrahydropyridine) is a chemical that is related to the opioid analgesic drugs. MPTP causes Parkinsonian side-effects. This occurs when MPTP is metabolized into MPP+, which kills neurons in a part of the brain called the substantia nigra. MPP+ interferes with mitochondria metabolism which leads to cell death and causes the build up of free radicals, toxic molecules that contribute further to cell destruction. MPTP has abilities to effect neuronal death in dopaminergic cells. Such effects lead to gross depletion of dopaminergic neurons which has severe implications on cortical control of complex movements.

GENERAL EXPERIMENTAL DESIGN

Experiment 1a

Determining that MPTP Causes Continued Cell Death

Control (non tg) and transgenic mice receive five intraperitoneal injections of MPTP-HCl (23 gauge needle, 20 mg/kg of free base; Sigma, St. Louis, Mo., USA) dissolved in sterile 0.9% saline at 2-h interval in 1 day. Control animals receive five intraperitoneal injections of 0.9% saline. This results in a ≈60% lesion of the SN. 20 C57BL6, 10 control and 10 hA53T tg are used to establish the precise dose of toxin at 2 weeks. Animals are allowed to recover for 1 week, 2 weeks, 1 month, 12, months and 18 months. The animals are killed and the brains removed for histological (stereological) and biochemical analysis.

Experiment 2

Determining Whether Test Drug Reduces MPTP Induced Cell Death

Animals are treated as described above. They are treated with test drug 2 days after MPTP injection until death. Test drug is given by oral gavage at a daily dosage of 30 mg/kg. The time of killing the animals is dependant on the analysis of Experiment 1, normally one month or less.

Drug Administration

Drugs are administered by oral gavage, at a daily dosage of 30 mg/kg.

Behavioral Monitoring:

Mice are assessed at prior to killing the mice for histological analysis.

Rotarod

Motor coordination and strength are assessed using the rotarod. The rotarod consists of a plastic rotating rod of 3.6 cm axial diameter partitioned by metal disks into five sections to allow the testing of multiple mice simultaneously. Mice are trained on two sessions where the rotation speed is ramped from 0-30 rpm over 5 min and one training session where rotation is a constant 16 rpm for 5 min. Within two days of training, animals are formally assessed on the rotarod rotating at 16 rpm for a maximum of 3 min: the time to fall on this single test is the recorded data point.

Pole Test

The pole is a 700 mm long, 5 mm diameter, wooden rod. The rod is supported at its base and held vertical. The total walking distance for the mice is 550 mm. The time taken for the mouse to descend the pole is measured with a maximum time of 120 s. If a mouse falls, the time is scored as 120 s.

TABLE 6

MPTP data

| Treatment | Behaviour Pole Test, Open field | SN cell counts % of SSV (cells +/− SD) | Mice in trial (n=) |
|---|---|---|---|
| SSV Control<br>F4267<br>(30 mg/kg) | NA | Unlesioned<br>285.74% (6184.72 ± 197.07)<br>SSV<br>0% (2164.43 ± 320.79)<br>F4267<br>53.94% (3331.96 ± 262.97) | 30 |
| SSV<br>CQ | NA | 7 Day Treatment<br>SSV<br>35.2% (2180 +/− 236)<br>CQ<br>44% (2725 +/− 257) | 30 |
| SSV, F4268,<br>L-DOPA<br>(20 mg/kg)<br>Selegiline | Pole test behaviour cannot be analysed | Unlesioned<br>352.74% (6184.72 ± 197.07)<br>SSV<br>0% (1753 +/− 323)<br>F4268<br>74.83% (3065 ± 387)<br>L-DOPA<br>10.39% (1935 ± 296) | 50 |
| SSV, F4268<br>(30 mg/kg),<br>L-DOPA<br>(20 mg/kg)<br>Selegiline<br>(1 mg/kg) | Pole test:<br>Unlesioned<br>26.95% (2.13 ± 1.15)<br>SSV<br>0% (2.92 ± 1.88)<br>F468<br>−25.38% (3.66 ± 1.87)<br>L-DOPA<br>−205.29% (8.91 ± 5.25)<br>Selegiline<br>−198.93% (8.73 ± 7.95)<br>F4268/L-DOPA<br>−4.21% (2.77 ± 1.10) | Unlesioned<br>320.59% (6184.72 ± 197.07)<br>SSV<br>0% (1929.14 ± 355.82)<br>F4268<br>64.00% (3163.87 ± 611.27)<br>L-DOPA<br>4.50% (2015.91 ± 729.87)<br>Selegiline<br>39.2% (2754.62 ± 461.23)<br>F4268/L-DOPA<br>55.21% (2721.94 ± 419.73) | 60 |
| SSV Control<br>F4486<br>(30 mg/kg)<br>F4495<br>(30 mg/kg),<br>F4496<br>(30 mg/kg) | Unlesioned<br>26.95% (2.13 ± 1.15)<br>SSV<br>0% (2.92 ± 1.88)<br>F4486<br>38.46% (1.81 ± 0.80)<br>F4495<br>18.32% (2.26 ± 0.82)<br>F4496<br>38.61% (1.79 ± 1.13) | Unlesioned<br>289.87% (6184.72 ± 197.07)<br>SSV<br>0% (2133.59 ± 162.57)<br>F4486<br>24.11% (2647.97 ± 814.44)<br>F4495<br>50.33% (3207.49 ± 678.16)<br>F4496<br>69.62% (3619.04 ± 613.47) | 50 |
| SSV Control<br>F4095<br>(30 mg/kg)<br>F4161<br>(30 mg/kg),<br>F4391<br>(30 mg/kg) | Unlesioned<br>26.95% (2.13 ± 1.15)<br>SSV<br>0% (2.92 ± 1.88)<br>F4095<br>24.25% (2.21 ± 0.89)<br>F4161<br>2.55% (2.85 ± 1.63)<br>F4391<br>9.96% (2.63 ± 1.10) | Unlesioned<br>284.73% (6184.72± 197.07)<br>SSV<br>0% (2172.12 ± 420.33)<br>F4095<br>12.15% (2436.00 ± 603.06)<br>F4161<br>28.05% (2781.33 ± 382.88)<br>F4391<br>25.18% (2719.11 ± 255.12) | 50 |

TABLE 6-continued

MPTP data

| Treatment | Behaviour Pole Test, Open field | SN cell counts % of SSV (cells +/− SD) | Mice in trial (n=) |
|---|---|---|---|
| SSV Control F4267 | NA | Unlesioned 220.39% (6184.72 ± 197.07) SSV 0% (2806.26 ± 329.26) F4267 53.77% (4315.11 ± 310.21) | 70 |
| SSV Control F4269 (30 mg/kg) | NA | Unlesioned 220.39% (6184.72 ± 197.07) SSV 0% (2806.26 ± 329.26) F4269 26.76% (3557.33 ± 556.55) | 70 |
| SSV Control F4385 | NA | Unlesioned 220.39% (6184.72 ± 197.07) SSV 0% (2806.26 ± 329.26) F4385 31.49% (3690.00 ± 919.10) | 70 |
| SSV Control F4268 | NA | Unlesioned 220.39% (6184.72 ± 197.07) SSV 0% (2806.26 ± 329.26) F4268 40.35% (3797.33 ± 562.78) | 70 |
| SSV Control F4495 (30 mg/kg) | NA | Unlesioned 220.39% (6184.72 ± 197.07) SSV 0% (2806.26 ± 329.26) F4495 45.45% (4081.78 ± 538.77) | 70 |
| SSV Control F4496 (30 mg/kg) | NA | Unlesioned 220.39% (6184.72 ± 197.07) SSV 0% (2806.26 ± 329.26) F4496 33.80% (3754.67 ± 619.05) | 70 |

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:

1. A compound of general formula I

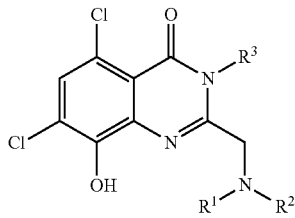

I in which $R^1$ is selected from H, optionally substituted $C_{1-6}$alkyl, optionally substituted $C_{3-6}$cycloalkyl and optionally substituted $C_{2-6}$alkynyl; $R^2$ is optionally substituted $C_{2-6}$alkynyl; or $R^1$ and $R^2$ together with the N atom to which they are attached form an optionally substituted 5- or 6-membered heterocyclyl which may contain at least one further heteroatom selected from N and O; and $R^3$ is selected from optionally substituted $C_{1-6}$alkyl and optionally substituted $C_{3-6}$cycloalkyl;

or pharmaceutically acceptable salts thereof.

2. A compound according to claim 1, in which the optional substituents are selected from $C_{1-4}$alkyl, optionally substituted aryl, halo, optionally substituted $C_{3-6}$cycloalkyl and optionally substituted 5- or 6-membered heterocyclyl containing at least one ring heteroatom selected from N and O.

3. A compound according to claim 1, in which $R^3$ is selected from methyl substituted with $C_{3-6}$cycloalkyl, methyl substituted with optionally substituted 5- or 6-membered heterocyclyl containing at least one ring heteroatom selected from N and O; substituted alkyl selected from ethyl, butyl, isobutyl, sec-butyl, tert-butyl, pentyl, neopentyl and hexyl; and optionally substituted $C_{3-6}$cycloalkyl.

4. A compound according to claim 1, in which $R^1$ is H and $R^2$ is optionally substituted $C_{2-6}$alkynyl.

5. A compound according to claim 1, in which $R^1$ is $C_{1-6}$alkyl and $R^2$ is $C_{2-6}$alkynyl.

6. A compound according to claim 1, in which $R^1$ and $R^2$ together with the N atom to which they are attached form an optionally substituted 5- or 6-membered heterocyclyl which may contain at least one further ring heteroatom selected from N and O.

7. A compound according to claim 1 which is a compound of formula Ia

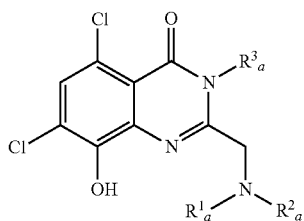

Ia in which
R$^1_a$ is selected from H and C$_{1-4}$alkyl;
R$^2_a$ is C$_{2-6}$alkynyl; or
R$^1_a$ and R$^2_a$ together with the N atom to which they are attached form an optionally substituted 5- or 6-membered heterocyclyl which may contain at least one further heteroatom selected from N and O; and
R$^3_a$ is C$_{1-6}$alkyl;
or pharmaceutically acceptable salts thereof.

8. A compound which is selected from the following:

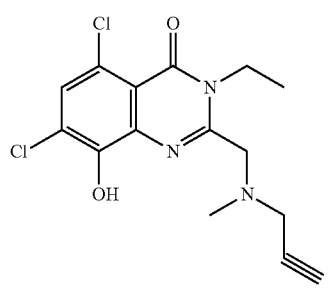

F4392

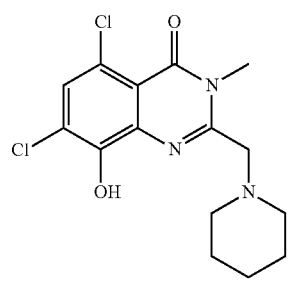

F4475

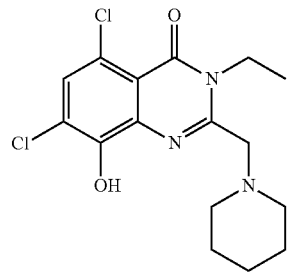

F4483 or pharmaceutically acceptable salts thereof.

9. A compound according to claim 1
in which
R$^3$ is optionally substituted C$_{3-6}$cycloalkyl
or pharmaceutically acceptable salts thereof.

10. A compound according to claim 9, in which R$^1$ is C$_{1-4}$alkyl.

11. A compound according to claim 1 which is a compound of formula Ic

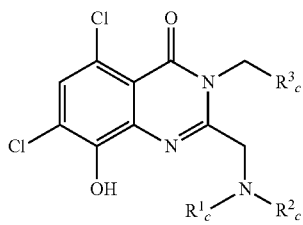

Ic in which
R$^1_c$ is selected from H and C$_{1-4}$alkyl;
R$^2_c$ is C$_{2-4}$alkynyl; or
R$^1_c$ and R$^2_c$ together with the N atom to which they are attached form an optionally substituted 5- or 6-membered heterocyclyl which may contain at least one further heteroatom selected from N and O; and
R$^3_c$ is selected from optionally substituted C$_{3-6}$cycloalkyl, optionally substituted aryl and optionally substituted 5- or 6-membered heterocyclyl containing at least one heteroatom selected from N and O;
or pharmaceutically acceptable salts thereof.

12. A compound according to claim 11, in which R$^3_c$ is aryl optionally substituted with halo.

13. A compound according to claim 11, in which R$^1_c$ is C$_{1-4}$alkyl and R$^2_c$ is C$_{2-6}$alkynyl.

14. A compound according to claim 11 which is selected from the following:

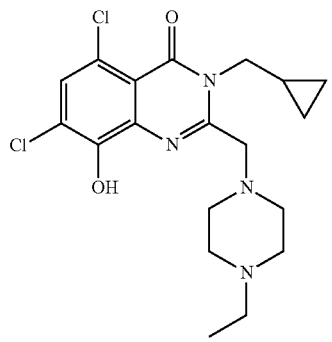

F4383

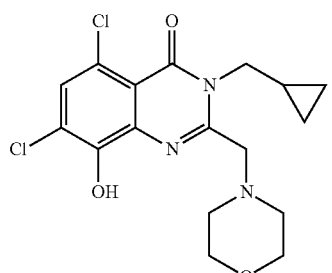

F4384

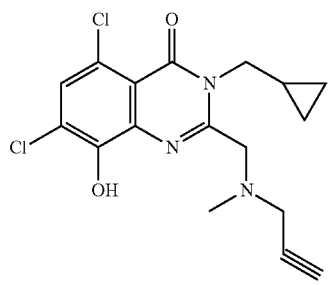

F4387

-continued

F4391

F4499 or pharmaceutically acceptable salts thereof.

15. The compound according to claim 1 in which $R^1$ and $R^2$ together with the N atom to which they are attached form an optionally substituted 5- or 6-membered heterocyclyl which may contain at least one further ring heteroatom selected from N and O.

16. The compound according to claim 1 wherein $R^1$ is selected from H, optionally substituted $C_{3-6}$cycloalkyl, and optionally substituted $C_{2-6}$alkynyl, optionally substituted $C_{1-6}$alkyl wherein the substituents on the alkyl are selected from $C_{2-6}$alkynyl, optionally substituted 5 or 6-membered heterocyclyl containing at least one ring heteroatom selected from N and O, and optionally substituted aryl; $R^2$ is optionally substituted $C_{2-6}$alkynyl; or $R^1$ and $R^2$ together with the N atom to which they are attached form an optionally substituted 5- or 6-membered heterocyclyl which may contain at least one further heteroatom selected from N and O; and $R^3$ is selected from optionally substituted $C_{1-6}$alkyl optionally substituted $C_{3-6}$cycloalkyl;

or pharmaceutically acceptable salts thereof.

17. A compound of general formula I

I in which $R^1$ is selected from H; substituted $C_{1-6}$alkyl, in which the substituents are selected from optionally substituted aryl, halo, optionally substituted $C_{3-6}$cycloalkyl and optionally substituted 5- or 6-membered heterocyclyl containing at least one ring heteroatom selected from N and O; optionally substituted $C_{3-6}$cycloalkyl and optionally substituted $C_{2-6}$alkynyl; $R^2$ is optionally substituted $C_{2-6}$alkynyl; or $R^1$ and $R^2$ together with the N atom to which they are attached form an optionally substituted 5- or 6-membered heterocyclyl which may contain at least one further ring heteroatom selected from N and O; and $R^3$ is selected from optionally substituted $C_{1-6}$alkyl and optionally substituted $C_{3-6}$cycloalkyl;

in which the optional substituents are selected from $C_{1-4}$alkyl, optionally substituted aryl, halo, optionally substituted $C_{3-6}$cycloalkyl and optionally substituted 5- or 6-membered heterocyclyl containing at least one ring heteroatom selected from N and O;

or pharmaceutically acceptable salts thereof d.

18. A pharmaceutical composition comprising a compound according to claim 1 and a pharmaceutically acceptable carrier thereto.

19. A process for the preparation of the compound of formula I

I in which $R^1$ is selected from H, optionally substituted $C_{1-6}$alkyl, optionally substituted $C_{3-6}$cycloalkyl and optionally substituted $C_{2-6}$alkynyl; $R^2$ is optionally substituted $C_{2-6}$alkynyl; or $R^1$ and $R^2$ together with the N atom to which they are attached form an optionally substituted 5- or 6-membered heterocyclyl which may contain at least one further heteroatom selected from N and O; and $R^3$ is selected from optionally substituted $C_{1-6}$alkyl and optionally substituted $C_{3-6}$cycloalkyl or pharmaceutically acceptable salts thereof (b);

which process comprises the steps of:

(i) cyclisation of a compound of formula III in the presence of a source of a leaving group

III in which $R^8$ is H or a protecting group to prepare a compound of formula IV

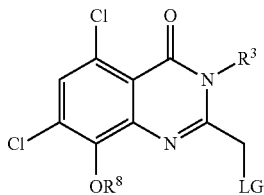

in which
LG is a leaving group; and
  (ii) aminating the compound of formula IV with a source of $NR^1R^2$ and deprotecting when $R^8$ is a protecting group, thereby forming a compound of formula I.

20. A process for the preparation of the compound of formula I

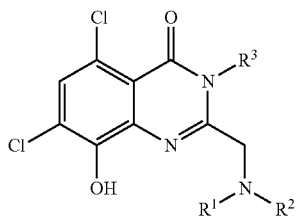

in which
$R^1$ is selected from H, optionally substituted $C_{1-6}$alkyl, optionally substituted $C_{3-6}$cycloalkyl and optionally substituted $C_{2-6}$alkynyl; $R^2$ is optionally substituted $C_{2-6}$alkynyl; or
$R^1$ and $R^2$ together with the N atom to which they are attached form an optionally substituted 5- or 6-membered heterocyclyl which may contain at least one further heteroatom selected from N and O; and
$R^3$ is selected from optionally substituted $C_{1-6}$alkyl and optionally substituted $C_{3-6}$cycloalkyl or pharmaceutically acceptable salts thereof
(b);
which process comprises the steps of:
  (i) cyclisation of a compound of formula V in the presence of a source of $NR^3$

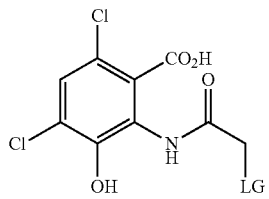

in which
LG is a leaving group
to prepare a compound of formula VI

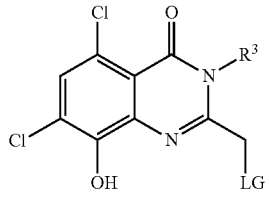

and
  (ii) aminating the compound of formula VI with a source of $NR^1R^2$, thereby forming a compound of formula I.

* * * * *